US 9,222,866 B2

(12) United States Patent
Cline et al.

(10) Patent No.: US 9,222,866 B2
(45) Date of Patent: Dec. 29, 2015

(54) EVALUATION OF GROUND SURFACE HARDNESS

(75) Inventors: Van Willis Cline, St. Paul, MN (US); Kathleen Sue Rice, Faribault, MN (US); Troy David Carson, Richfield, MN (US)

(73) Assignee: The Toro Company, Bloomington, MN (US)

( * ) Notice: Subject to any disclaimer, the term of this patent is extended or adjusted under 35 U.S.C. 154(b) by 279 days.

(21) Appl. No.: 13/409,979

(22) Filed: Mar. 1, 2012

(65) Prior Publication Data

US 2013/0055797 A1    Mar. 7, 2013

Related U.S. Application Data

(60) Provisional application No. 61/447,813, filed on Mar. 1, 2011.

(51) Int. Cl.
*G01N 3/42* (2006.01)
*G01N 3/40* (2006.01)
*G01N 3/303* (2006.01)
*G01N 33/24* (2006.01)

(52) U.S. Cl.
CPC ............ *G01N 3/40* (2013.01); *G01N 3/303* (2013.01); *G01N 33/24* (2013.01)

(58) Field of Classification Search
USPC .................... 73/78–85, 12.06, 12.12
See application file for complete search history.

(56) References Cited

U.S. PATENT DOCUMENTS

| 4,627,096 | A | * | 12/1986 | Grattoni et al. | 382/141 |
| 5,390,535 | A | * | 2/1995 | Smock et al. | 73/79 |
| 5,736,631 | A | * | 4/1998 | Dixon et al. | 73/12.06 |
| 6,807,841 | B1 | * | 10/2004 | Chen et al. | 73/12.06 |
| 6,892,564 | B2 | * | 5/2005 | Ishikawa | 73/12.06 |
| 6,925,858 | B2 | * | 8/2005 | Miles et al. | 73/84 |
| 7,137,285 | B2 | * | 11/2006 | Stroppiana | 73/12.13 |
| 2011/0203356 | A1 | * | 8/2011 | Scherbring | 73/84 |

FOREIGN PATENT DOCUMENTS

| AU | 2008100890 A4 | 11/2008 |
| FR | 2629846 A1 | 10/1989 |
| WO | 2004003301 A1 | 1/2004 |

OTHER PUBLICATIONS

ASTM International, "Standard Specification for Shock-Absorbing Properties of North American Football Field Playing Systems as Measured in the Field," 1999, 4 pages.
ASTM International, Standard Test Method for Shock-Absorbing Properties of Playing Surface Systems and Materials, 2002, 4 pages.

(Continued)

*Primary Examiner* — Hezron E Williams
*Assistant Examiner* — Xin Zhong
(74) *Attorney, Agent, or Firm* — Merchant & Gould P.C.

(57) ABSTRACT

Evaluating ground surface hardness for a site involves using a mobile data collection device to automatically drop an object including an accelerometer onto a ground surface at sample locations spaced at regular intervals within the site. The acceleration of the object is detected with the accelerometer as the object impacts the ground surface at the sample locations. A value is generated representative of ground surface hardness for each of the sample locations. Evaluation using a handheld hardness measurement device is also disclosed.

21 Claims, 16 Drawing Sheets

(56) References Cited

OTHER PUBLICATIONS

ASTM International, "Standard Test Method for Measuring Shock-Attenuation Characteristics of Natural Playing Surface Systems Using Lightweight Portable Apparatus," 1996, 5 pages.

ASTM International, "Standard Test Methods for Comprehensive Characterization of Synthetic Turf Playing Surfaces and Materials," 2003, 14 pages.

Humboldt Construction Materials Testing Equipment, "Clegg Impact Soil Tester," Feb. 28, 2011, 1 page.

Layfayette Instrument, "10 kg Clegg Impact Soil Tester," Feb. 28, 2011, 2 pages.

Layfayette Instrument, "20 kg Clegg Impact Soil Tester," Feb. 28, 2011, 2 pages.

Tru Firm, "New Impact Measurement and Analysis System for Golf Courses and Sports Field Surfaces," Mar.-Apr. 2009, 1 page.

Australian Government; Patent Examination Report No. 1 for Application No. 2012201262; Feb. 5, 2014; 7 pages.

Australian Patent Office, Patent Examination Report No. 2 for application No. 2012201262 dated Mar. 30, 2015, 6 pages.

\* cited by examiner

| PT No | Hardness (Gmax) | GPS Coord. | Moisture | Compaction | ETC. |
|---|---|---|---|---|---|
| 1 | 105 | 44....°N 93....°W | M1 | C1 | |
| 2 | 111 | 44....°N 93....°W | M2 | C2 | |
| 3 | 114 | 44....°N 93....°W | M3 | C3 | |
| ... | ... | | ... | ... | ... |

FIG. 5

|  | MOISTURE DATA | |
|---|---|---|
|  | TOO DRY | TOO WET |
| TOO HARD | INCREASE IRRIGATION | SOFTEN |
| TOO SOFT | HARDEN | DECREASE IRRIGATION |

HARDNESS DATA

FIG. 9

EVALUATION OF GROUND SURFACE HARDNESS

CROSS-REFERENCE TO RELATED APPLICATIONS

This application claims priority to U.S. Ser. No. 61/447,813, filed on Mar. 1, 2011, and titled EVALUATION OF GROUND SURFACE HARDNESS, the disclosure of which is hereby incorporated by reference in its entirety.

BACKGROUND

Ground surface hardness refers to a measure of the deceleration of an object upon impact with the surface. The units of deceleration can be expressed as G, which is the ratio of the magnitude of deceleration during impact to the acceleration of gravity. The maximum value of G encountered during impact is sometimes referred to as $G_{MAX}$.

The hardness of an athletic field can be a factor to consider in evaluating the safety of the athletic field. In some sports, such as football, contact with the ground surface is likely. Knowledge of the hardness of the field is useful in determining the relative safety of the field, and in comparing the hardness of the field with the hardness of other fields.

On the other hand, it is sometimes desirable to have a relatively hard ground surface. On a putting green, for example, a harder ground surface is less prone to damage when hit by golf balls, and can require less water for irrigation.

SUMMARY

In general terms, this disclosure is directed to systems and methods for evaluating ground surface hardness of a site.

One aspect is a method of evaluating ground surface hardness for a site, the method comprising: using a mobile data collection device to automatically drop an object including an accelerometer onto a ground surface at sample locations spaced at regular intervals within the site; detecting acceleration of the object with the accelerometer as the object impacts the ground surface at the sample locations; and generating a value representative of ground surface hardness for each of the sample locations.

Another aspect is a mobile data collection device comprising: a mobile surface hardness measurement device including a hammer and configured to automatically drop the hammer including an accelerometer onto a ground surface at sample locations spaced at regular intervals within a site and to detect acceleration of the hammer as the hammer impacts the ground surface and generate acceleration data; and a computing device configured to evaluate the acceleration data to generate a value representative of ground surface hardness for each of the sample locations.

A further aspect is a method of evaluating soil hardness, the method comprising: collecting ground surface hardness data points for a site; evaluating the ground surface hardness data points to identify at least one region of the site having an undesirable ground surface hardness condition; and prescribing a treatment for the undesirable ground surface hardness condition at the at least one region.

Another aspect is a ground surface hardness evaluation system, comprising: a processing device; and a computer storage device, the computer storage device storing data instructions, which when executed by the processing device, cause the processing device to: evaluate ground surface hardness data points to identify at least one region of a site having an undesirable ground surface hardness condition; and prescribe a treatment for the undesirable ground surface hardness condition at the at least one region.

A further aspect is a method of displaying ground surface hardness of a site, the method comprising: displaying a map of the site; and identifying a plurality of ground surface hardness data points on the map with a graphical element, wherein the graphical element visually indicates a magnitude of ground surface hardness values associated with the ground surface hardness data points.

Yet another aspect is a method of collecting data points, the method comprising: measuring ground surface hardness values at a plurality of locations of a site using a mobile surface hardness measurement device pulled behind a vehicle; and storing the measured ground surface hardness values in a computer storage medium.

BRIEF DESCRIPTION OF THE DRAWINGS

FIG. 5 is a table storing data collected by the data collection operation shown in FIG. 4.

FIG. 9 illustrates an example method of prescribing treatment using hardness data.

DETAILED DESCRIPTION

Figure 1:
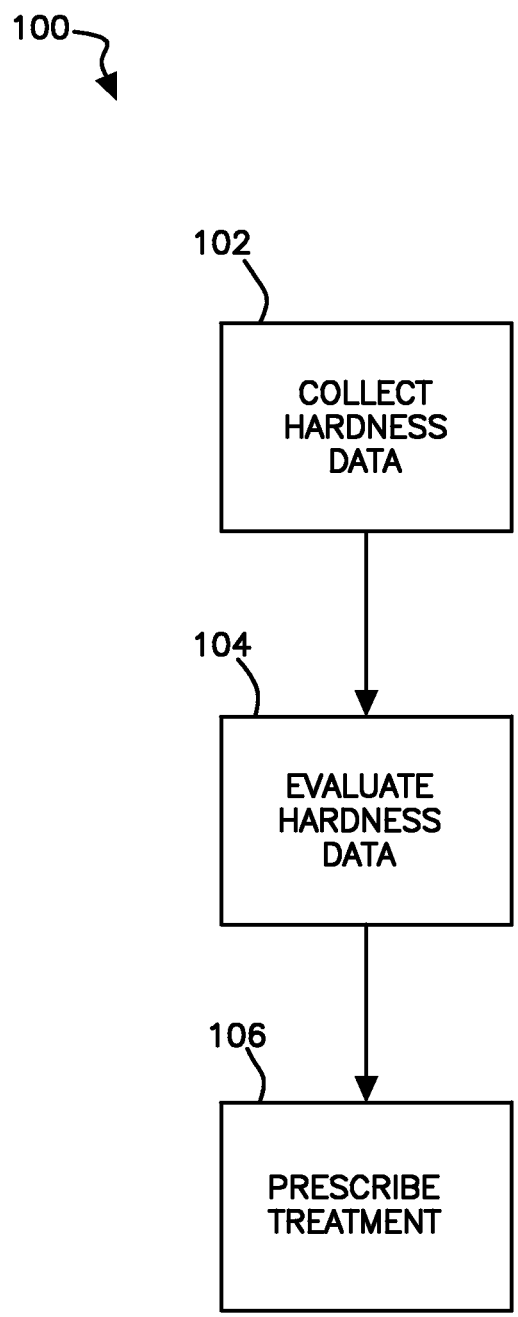
FIG. 1 is a flow chart illustrating an example method of evaluating ground surface hardness.

Various embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims.

FIG. 1 is a flow chart illustrating an example method 100 of evaluating ground surface hardness. In this example, the method 100 includes a data collection operation 102, a data evaluation operation 104, and a treatment prescription operation 106.

The data collection operation 102 involves the collection of ground surface hardness data at a site. The site typically includes a playing surface that is configured for the playing of a sport or other activity. An example of a site is a playing field, such as a field (e.g., a football field, a soccer field, a baseball field), a track (e.g., a horse track, a running track), a golf course (e.g., the putting green, fairway, rough, or tee box). Other sites are also used in other embodiments.

In some embodiments, the ground surface at the site includes turf. Turf includes both natural turfgrass as well as synthetic turf systems. Turfgrass is a type of vegetation that is commonly used in lawns. Turfgrass is also commonly used on a variety of playing surfaces.

Synthetic turf systems are often formed over a foundation of concrete, asphalt, or crushed rock, and include at least a carpet layer that simulates natural turfgrass. In some embodiments, one or more padding layers are included between the foundation layer and the carpet layer. In addition, a filler is sometimes provided on the carpet layer. An example of the filler is a combination of sand and rubber particles, such as ground up pieces of tires or athletic shoes.

The hardness of a ground surface can be measured by a ground surface hardness measurement device. Examples of ground surface hardness measurement devices are illustrated and described in more detail with reference to FIGS. 2-3.

Figure 4:
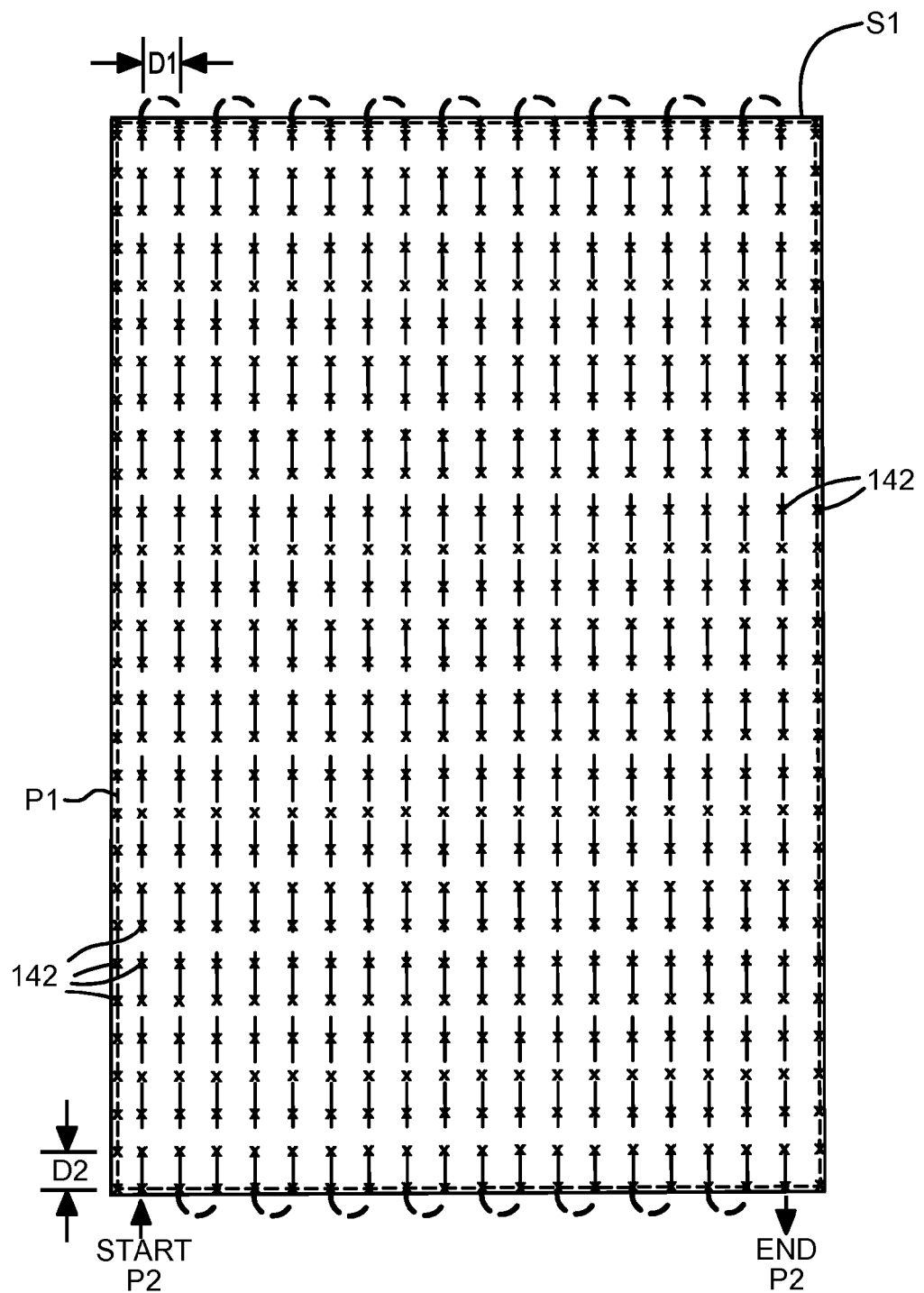
FIG. 4 is a schematic diagram of an example site, illustrating a data collection operation of the method shown in FIG. 1.

In some embodiments, the ground surface hardness measurement device is used to collect data at many different points of the ground surface. An example is shown in FIG. 4, which illustrates paths for collecting ground surface hardness data. For example, in some embodiments, the data points are collected along approximately a 10' by 10' grid, although other embodiments utilize other data collection dimensions and arrangements.

In addition to ground hardness data, some embodiments also collect additional data. Examples of other data include soil moisture data, location data (such as global positioning system data), irrigation system location data, soil penetration data, spectrometer data, or other data identifying one or more characteristics of, or related to, the ground surface.

The data evaluation operation 104 is performed to evaluate the data after the ground hardness data has been collected. For example, data processing is performed to interpolate the data, and to plot the data on a map of the site to permit visual inspection and evaluation of the ground hardness data. The data evaluation operation 104 is described in more detail with reference to FIGS. 6-9.

In some embodiments, evaluation of the ground hardness data includes a comparison of the ground hardness data with other data. For example, the ground hardness data can be compared to soil moisture data, to determine whether the ground hardness is correlated to soil moisture conditions, or uncorrelated with soil moisture conditions.

In some embodiments, the data evaluation operation 104 identifies undesirable soil hardness conditions, such as regions of the site that are too hard, or regions of the site that are too soft.

In some embodiments, the data evaluation operation 104 generates one or more scores based at least in part upon the ground hardness data. In some embodiments, one or more scores are generated representing the relative hardness of at least portions of the ground surface. Examples are described in more detail herein with reference to FIGS. 10-16.

In some embodiments, the treatment prescription operation 106 is then performed following the data evaluation operation 104 to generate a treatment plan for undesirable soil hardness conditions that have been identified. The treatment prescription operation 106 is described in more detail with reference to FIGS. 8-9. Some embodiments do not include the treatment prescription operation 106.

A variety of options are available to treat ground surface hardness conditions. Some options include physical cultivation (e.g., compaction, vibration, aerification, tilling, or fluffing), moisture content adjustment (e.g., increasing or decreasing irrigation), ground surface composition adjustment (e.g., adjusting the proportions of clay, sand, organic matter, or various possible synthetic materials), or the removal of undesired matter such as rocks, tree roots, and the like.

Figure 2:
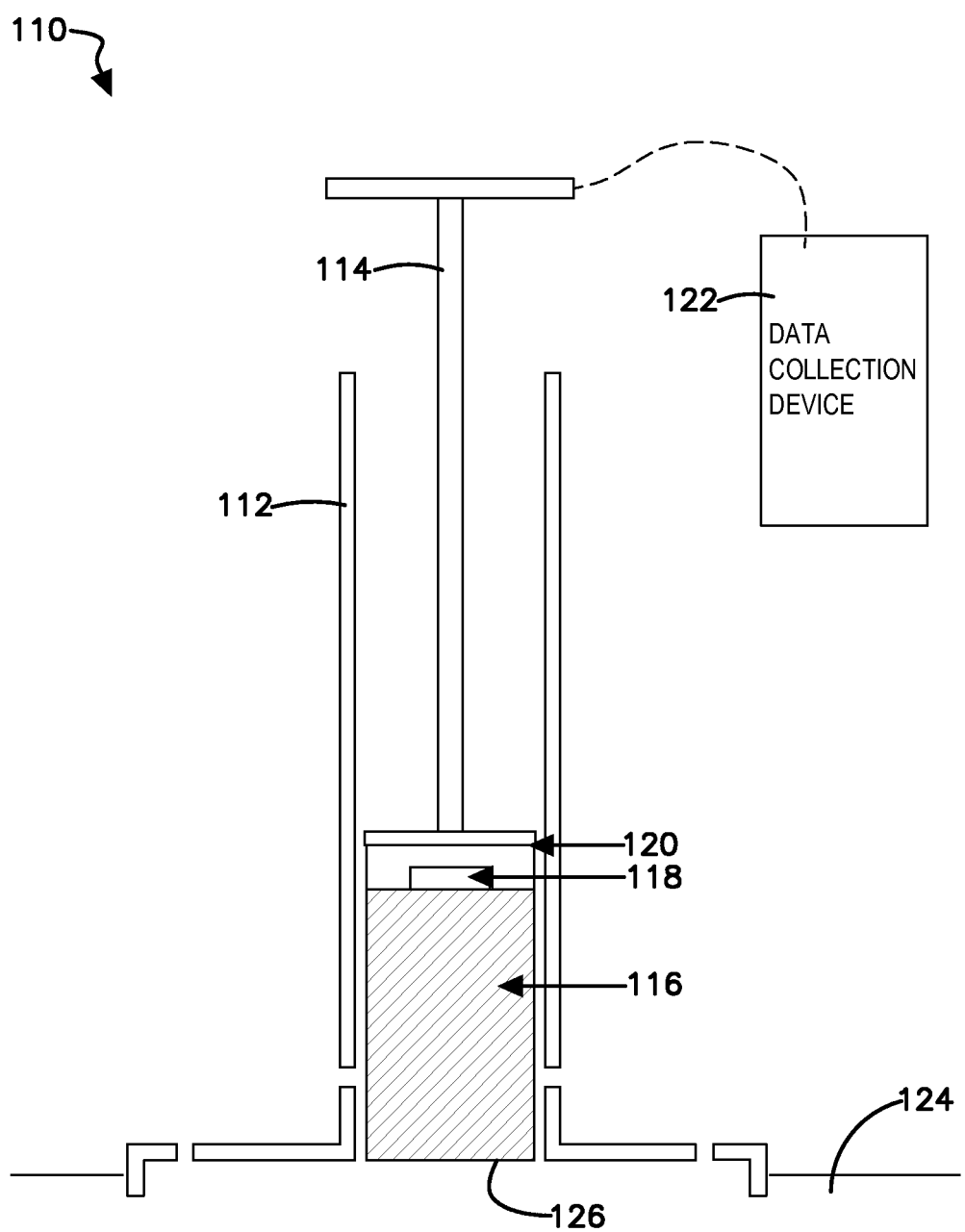
FIG. 2 is a cross-sectional diagram of an example hardness measurement device.

FIG. 2 is a cross-sectional diagram of an example hardness measurement device 110, and more specifically an example of a handheld hardness measurement device. The example hardness measurement device 110 includes a guide tube 112, a movable sensor 114, and a data collection device 122.

The guide tube 112 is typically a cylindrical tube having a hollow interior. A base plate is provided in some embodiments to support the guide tube 112 on a ground surface, and can include flanges for engaging with the ground. Vent holes are provided in some embodiments to permit air to move in and out of the guide tube 112 without interfering with the movement of the movable sensor 114.

The movable sensor 114 includes a missile body 116 having an exterior shape that permits the missile body 116 to slide up and down within the guide tube 112. In some embodiments, missile body 116 has a predetermined weight, such as 2.25 kg.

The movable sensor 114 also includes an accelerometer 118 that detects the acceleration of the missile 116 as it moves through the guide tube and impacts the ground 124. The movable sensor 114 includes a drop height indicator mark 120 on an exterior surface.

In operation, the guide tube 112 is placed onto a ground surface at a site where the ground hardness is to be measured. The moveable sensor 114 is inserted into the guide tube 112, or if already in the guide tube 112, is raised and positioned so that the drop height indicator mark 120 is aligned with the top of the guide tube 112. The moveable sensor 114 is then released, and is pulled rapidly toward the ground 124 by the force of gravity. The missile body 116 then proceeds through the guide tube 112 until the bottom surface of the missile body 116 impacts the ground 124. Upon impact, the missile body 116 decelerates rapidly until it comes to rest on the ground surface 124. The accelerometer records the acceleration of the missile body 116 (including the deceleration upon impact) and the acceleration data is supplied to the data collection device 122, which records the data in memory. In some embodiments, the data collection device 122 records the data in G's, by computing a ratio of the magnitude of deceleration during impact to the acceleration of gravity. In some embodiments, the data collection device 122 records the maximum value of G encountered during impact, which is sometimes referred to herein as the $G_{MAX}$.

Examples of the hardness measurement device 110 or a portion of the hardness measurement device 110 is a Clegg impact soil tester, such as model H-4196A distributed by Humboldt Manufacturing Co. of Shiller Park, Ill., and models 95056A (20 kg), 95055A (10 kg), and 95045A (2.25 kg) Clegg impact soil testers distributed by Lafayette Instrument of Lafayette, Ind. Another example of a hardness measurement device 110 is or includes the TruFirm system available from the United States Golf Association of Far Hills, N.J.

The missile body 116 can be selected from a variety of different configurations. In one example, the missile body 116 has a contact surface 126 having a substantially flat face, as shown in FIG. 2. In another possible embodiment, the contact surface 126 has a curved or rounded face, such as in the shape of a half-sphere. The weight (or mass) of the missile body 116 can be selected from a variety of different weights, such as in a range from about 1 pound to about 50 pounds, and in another example in a range from about 2 pounds to about 20 pounds. Other weights can be used in other embodiments. Preferably the weight and size is selected to mimic an impact of interest. For example, a weight and size can be selected that approximate the size and shape of a human head or a helmet worn on a human head to mimic the impact of a human head on the ground surface. Another example utilizes a missile body 116 having the size and shape of a golf ball.

In order to accurately compare one measurement (or set of measurements) with another measurement (or set of measurements) the configuration of the missile body 116 that is used for each measurement can be important. For example, in order to be able to accurately compare measurements taken at one site with measurements taken at another site, it would be preferable that approximately the same type of hardness measurement device 110 and missile body 116 (e.g., size, shape, and weight) be used for both fields.

When different hardness measurement devices 110 are used, some embodiments operate to normalize the data so that the measurements can be appropriately compared. For example, if one set of measurements is collected with a 10 kg missile body 116 and another set of measurements is collected with a 20 kg missile body 116, a predetermined formula can be used to generate an estimate of the measurements that would have been collected had the same missile body 116 been used. For example, the measurements collected with a 20 kg missile body can be converted into an estimate of the measurements that would have been collected with a 10 kg missile body using the predetermined formula. The estimated measurements can then be used for subsequent evaluation so that the two sets of data can be appropriately compared with each other.

Figure 3:
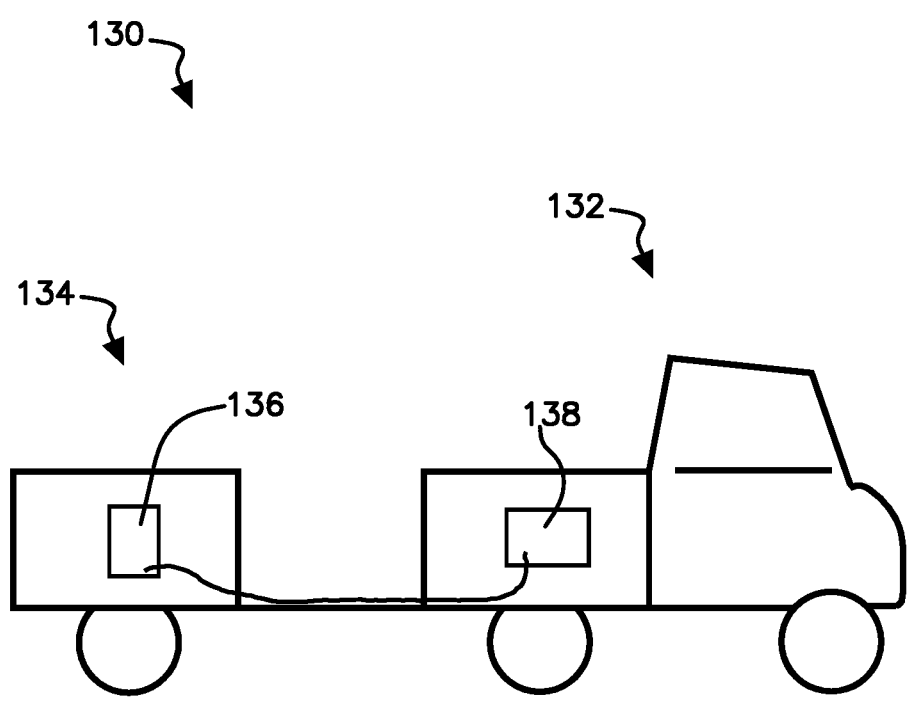
FIG. 3 is a block diagram of an example mobile data collection device including a mobile surface hardness measurement device.

FIG. 3 is a block diagram of an example mobile data collection device 130. The mobile data collection device 130 includes, for example, a data collection vehicle 132, and a mobile surface hardness measurement device 134.

The data collection vehicle 132 includes, for example, a frame, a body, wheels, a motor, a power source, a trailer hitch, and a computing device 138. Examples of the data collection vehicle 132 include a golf cart, a tractor, a truck, an all-terrain vehicle (ATV), a car, or other vehicle.

The data collection vehicle 132 can be coupled to the mobile surface hardness measurement device 134, such as by a ball and hitch coupling, or other suitable joint, to permit the measurement device 134 to be towed by the data collection vehicle 132.

However, in another possible embodiment the data collection vehicle 132 and the measurement device 134 are a single machine. For example, in some embodiments the mobile hardness measurement device 134 includes one or more motors for moving the mobile hardness measurement device 134 across the site. In another example embodiment, the mobile hardness measurement device 134 is a part of or connected to the data collection vehicle 132.

The mobile hardness measurement device 134 can alternatively be pushed or towed by a person or animal.

Examples of the measurement device 134 are disclosed in U.S. Publ. No. 2011/0203356 (U.S. Ser. No. 13/035,937), filed on Feb. 26, 2011, and titled Mobile Turf Instrument Apparatus Having Droppable Hammer Type Accelerometer Carried on Rotating Arm, the disclosure of which is hereby incorporated by reference in its entirety.

In some embodiments, the measurement device 134 includes a moveable sensor 136, such as including a hammer and accelerometer, which can be operated to repeatedly measure and collect hardness measurements as the measurement device 134 is moved along the site. Data from the movable sensor 136 is supplied to a computing device 138 where the data is stored in a memory device. The computing device 138 can be on the data collection vehicle 132, as shown in FIG. 3, or alternatively on the measurement device 134. Examples of a suitable hammer include the missile body 116 described herein with reference to FIG. 3.

The accelerometer records the acceleration of the hammer (including the deceleration upon impact) and the acceleration data is supplied to the computing device 138, which records the data in memory. Some embodiments record acceleration data points at regular intervals, such as at about 20 kHz or about 7 kHz (although other frequencies can be used in other embodiments). In some embodiments, the computing device 138 records the data in G's, by computing a ratio of the magnitude of deceleration during impact to the acceleration of gravity. In some embodiments, the computing device 138 records the maximum value of G encountered during impact, which is sometimes referred to herein as $G_{MAX}$. Additional values can also be computed from the acceleration data points. For example, the data points can be integrated to compute velocity data. The velocity data can also be integrated to compute displacement data.

A large amount of data can be collected when sampling at a relatively high frequency, such as 20 kHz. As a result, in some embodiments the acceleration data is discarded after one or more of these values have been computed from the acceleration data to reduce the amount of storage space required to store the data. In some embodiments the computations are performed by the computing device 138, which may be part of the data collection vehicle 132 or the mobile hardness measurement device 134.

FIG. 4 is a schematic diagram of an example site S1, illustrating one example of the data collection operation 102, shown in FIG. 1. The example illustrates data collection paths P1 and P2 for collecting data at data points 142.

In this example, site S1 is a generally rectangular athletic field, such as a football or soccer field. Other examples of sites S1 include lacrosse fields, baseball fields, rugby fields, race tracks (e.g., horse and dog race tracks), and the like.

Data is collected by sampling the site S1 at multiple locations. In some embodiments, a large number of data points 124 (such as more than 10, more than 50, or more than 100), are obtained by using a mobile surface hardness measurement device 134, such as shown in FIG. 3. Use of the mobile surface hardness measurement device 134 permits the collection of data much more quickly than if a handheld hardness measurement device 110 is used, such as shown in FIG. 2. However, either device 134 or 110 can be used.

In one example, a path P1 is followed to collect data about the perimeter of the site S1. The data includes at least ground surface hardness data. In some embodiments, one or more additional pieces of data are also collected, such as GPS coordinates, soil moisture measurements, soil penetration measurements, and any other data that can be measured or detected. The path P1 is particularly helpful if GPS data is collected, to identify the coordinates of the perimeter of site S1. For example, if samples were taken outside of the perimeter, such as when turning around between passes, the data located outside of the perimeter of site S1 can be removed from the data set or otherwise excluded from evaluation during the data evaluation operation 104, shown in FIG. 1. Some embodiments do involve collecting data points along a path P1 about the perimeter of site S1.

A path P2 is followed in some embodiments to collect data within the perimeter of site S1. In this example, multiple passes are made across the site S1, which are spaced approximately a distance D1 from each other. The measurement device 134 is operated to collect data points along the path P2 at regular intervals, such that the data points 142 have a spacing of approximately a distance D2 from each other. In this way, a roughly regular and repeating pattern of samples are obtained throughout the site S1, so that samples across the entire ground surface (or one or more regions of the ground surface) of the site S1 are collected for evaluation.

In some embodiments, the distance D1 and the distance D2 are substantially equal. To provide an example, in some embodiments the distances D1 and D2 are in a range from about 5 feet to about 15 feet. In other possible embodiments, the distance D1 is different than the distance D2. For example, the distance D2 between data points is about 8 feet and the distance D1 between rows is in a range from about 10 feet to about 15 feet. Other embodiments include distances that are larger or smaller than these examples, such as in a range from about 1 foot to about 50 feet. Further, some embodiments do not include substantially regular and repeating patterns of data points 142.

In some embodiments, the spacing and locations of the one or more paths P2 is determined by characteristics of the site S1. For example, if the site S1 is a football field, the path P2 can be positioned relative to the yard lines. In an American football field, yard lines are typically provided at five yard intervals across the field. In one example, the rows of the path P2 are positioned at midpoints between yard lines (e.g., 2.5 yards, 7.5 yards, 12.5 yards, etc.). A benefit of taking measurements between yard lines is that it reduces the effect that paint may have on the hardness measurements. For example, the paint may slightly increase hardness measurements taken on a yard line. In another possible embodiment, at least some of the measurements are taken on the yard lines.

FIG. 5 is a table 160 storing collected data for data points 142, shown in FIG. 4. In one example, a table 160 is stored in a memory device of computing device 138 of data collection vehicle 132. In some embodiments, after the data points 142 are collected, the data is transferred from computing device 138 to a computer storage medium, such as a CD or flash drive, or to another computing device, such as across a network. In some embodiments, the data points 142 are stored on a surface hardness evaluation system, such as described in more detail with reference to FIGS. 6-7.

Table 160 stores data for each data point 142, such as shown in FIG. 4. The data includes at least ground surface hardness data 164. In this example, the data includes a point identification number 162, ground surface hardness data 164, GPS coordinates 166, moisture data 168, compaction data 170, and other possible data.

For example, the first of the data points 142 has a point identification number 162 of "1", a hardness value of "105," a GPS coordinate 166, a moisture value represented by M1, and a compaction value represented by C1. Data for the other data points 142 is similarly stored in table 160.

As discussed herein, additional data can be computed from the acceleration data, in addition to (or instead of) the $G_{MAX}$ hardness data 164, such as velocity or displacement.

Data can also be stored in other formats, other than a table format, such as a data file, a linked list, a database file, or any other desired data storage format.

Figure 6:
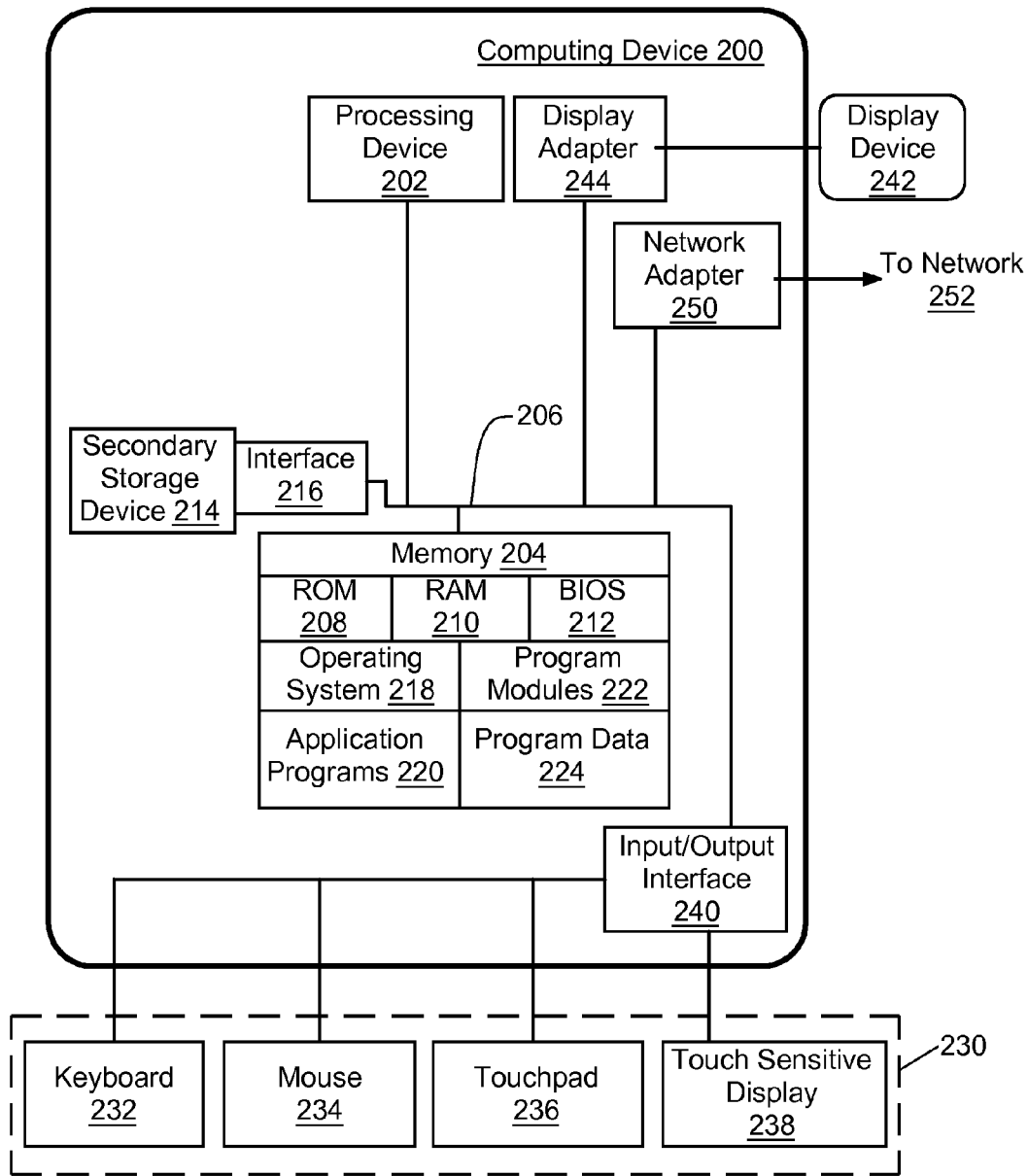
FIG. 6 is a schematic block diagram of an example computing device of an example surface hardness evaluation system.
Figure 7:
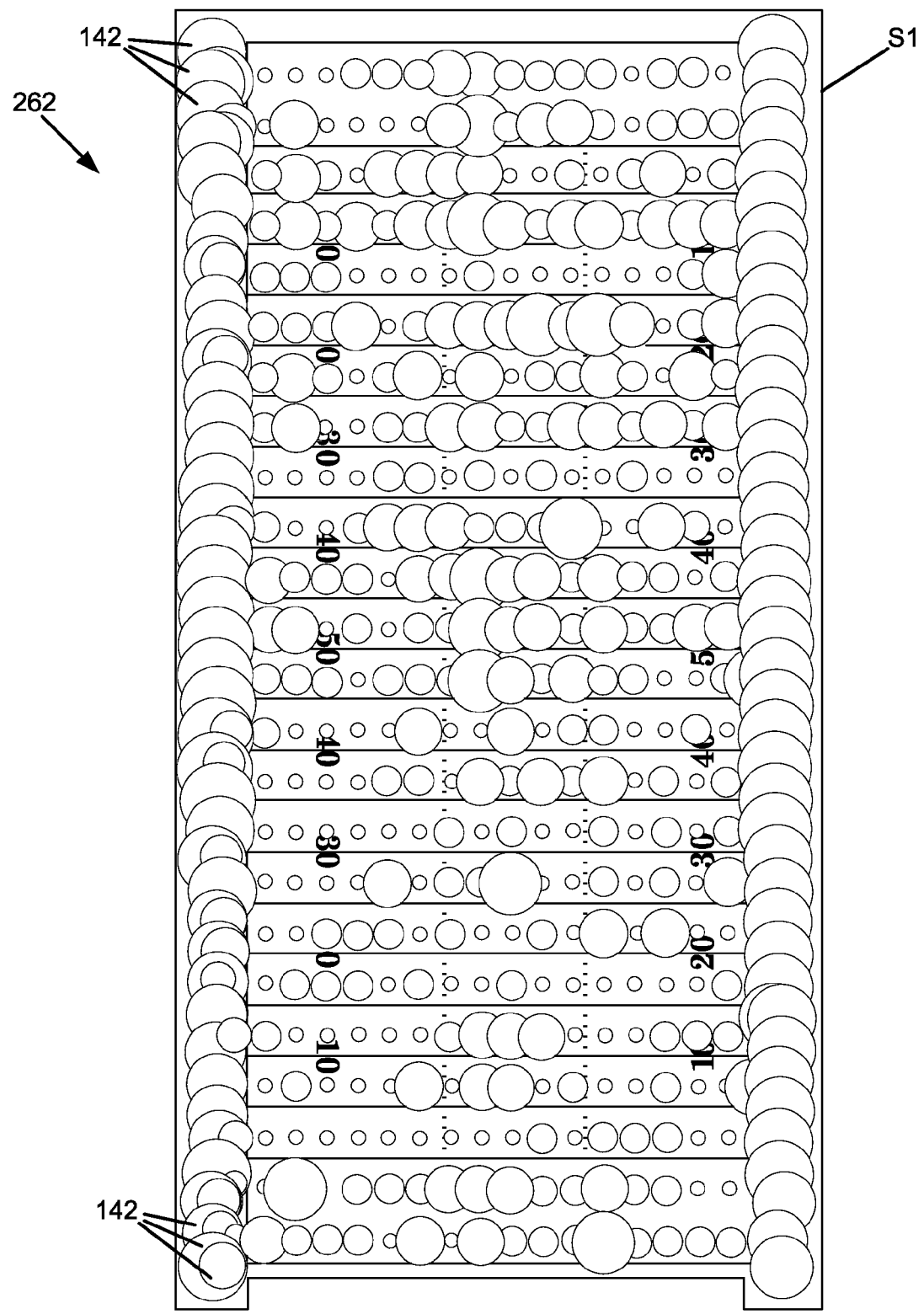
FIG. 7 is a map display graphically depicting collected data to permit visual evaluation of ground surface hardness values.

FIGS. 6-7 illustrate examples of the data evaluation operation 104, shown in FIG. 1, such as performed by a surface hardness evaluation system.

FIG. 6 is a schematic block diagram illustrating an example computing device 200 of an example surface hardness evaluation system. In addition, the example computing device 200 is also an example of a computing device that can be used to perform one or more of the methods, operations, computations, or processes discussed herein by other computing devices. For example, computing device 200 is an example of a computing device of a mobile data collection device, a computing device of an irrigation system, a server computing device, or a computing device operated by a client or customer. Because computing device 200 is a suitable example of these other computing devices, they will not be separately described in detail herein.

In one example embodiment, computing device 200 is a personal computer. Other embodiments include other computing devices 200, such as a tablet computer, a smart phone, a personal digital assistant (PDA), or other device configured to process data instructions. In some embodiments, computing device 200 is an example of programmable electronics. In another possible embodiment, two or more computing devices 200 collectively form at least a portion of the programmable electronics.

Computing device 200 includes, in some embodiments, at least one processing device 202 and memory 204. A variety of processing devices 202 are available from a variety of manufacturers, for example, Intel or Advanced Micro Devices. In some embodiments, the processing device 202 is configured to perform one or more methods or operations as defined by instructions stored in a memory device. Examples of such methods and operations are described herein.

Computing device 200 also includes, in some embodiments, at least one memory device 204. Examples of memory devices 204 include read-only memory 208 and random access memory 210. Basic input/output system 212, containing the basic routines that act to transfer information within computing device 200, such as during start up, is typically stored in read-only memory 208. Memory device 204 can be a part of processing device 202 or can be separate from processing device 202.

In this example, computing device 200 also includes system bus 206 that couples various system components including memory 204 to processing device 202. System bus 206 is one of any number of types of bus structures including a memory bus, or memory controller; a peripheral bus; and a local bus using any of a variety of bus architectures.

In some embodiments, computing device 200 also includes secondary storage device 214 for storing digital data. An example of a secondary storage device is a hard disk drive. Secondary storage device 214 is connected to system bus 206 by secondary storage interface 216. Secondary storage devices 214 and their associated computer readable media provide nonvolatile storage of computer readable instructions (including application programs and program modules), data structures, and other data for computing device 200.

Although the exemplary architecture described herein employs a hard disk drive as a secondary storage device, other types of computer readable media are included in other embodiments. Examples of these other types of computer readable media include magnetic cassettes, flash memory cards, digital video disks, Bernoulli cartridges, compact disc read only memories, digital versatile disk read only memories, random access memories, read only memories, or other memory devices.

A number of program modules can be stored in secondary storage device 214 or memory 204, including operating system 218, one or more application programs 220, other program modules 222, and program data 224. In some embodiments, program modules include data instructions that are stored in computer readable media (such as computer readable storage media). The data instructions, when executed by the processing device 202, cause the processing device 202 to perform one or more of the methods or operations described herein.

In some embodiments, a user provides inputs to the computing device 200 through one or more input devices 230. Examples of input devices 230 include keyboard 232, mouse 234, touchpad 236, and touch sensitive display 238. Other embodiments include other input devices 230. Input devices 230 are often connected to the processing device 202 through input/output interface 240 that is coupled to system bus 206. These input devices 230 can be connected by any number of input/output interfaces, such as a parallel port, serial port, game port, or a universal serial bus. Wireless communication between input devices and interface 240 is possible as well, and includes infrared, BLUETOOTH® wireless technology, 802.11a/b/g/n/z wireless communication, cellular communication, or other radio frequency communication systems in some possible embodiments.

In some embodiments, a display device 242, such as a monitor, liquid crystal display device, projector, or touch screen display device, is connected to system bus 206 via an interface, such as display adapter 244. In addition to display device 242, the computing device 200 can include various other peripheral devices (not shown), such as speakers or a printer. In some embodiments the display device 242 and touch sensitive display 238 are the same device.

When used in a local area networking environment or a wide area networking environment (such as the Internet), computing device 200 is typically connected to network 252 through a network interface or adapter 250. Other possible embodiments use other communication devices. For example, some embodiments of computing device 200 include a modem for communicating across network 252.

Computing device 200 typically includes at least some form of computer-readable media. Computer readable media include any available media that can be accessed by computing device 200. By way of example, computer-readable media include computer readable storage media and communication media.

The term computer readable media as used herein includes computer storage media. Computer storage media includes volatile and nonvolatile, removable and non-removable media implemented in any method or technology for storage of information, such as computer readable instructions, data structures, program modules, or other data. Computer readable storage media includes, but is not limited to, read-only memory 208, random access memory 210, electrically erasable programmable read only memory, flash memory or other memory technology, compact disc read only memory, digital versatile disks or other optical storage, magnetic cassettes, magnetic tape, magnetic disk storage or other magnetic storage devices, or any other medium that can be used to store the desired information and that can be accessed by computing device 200. In some embodiments, computer readable storage media is non-transitory media.

Communication media can be embodied by computer readable instructions, data structures, program modules or other data in a modulated data signal, such as a carrier wave or other transport mechanism and includes any information delivery media. The term "modulated data signal" refers to a signal that has one or more of its characteristics set or changed in such a manner as to encode information in the signal. By way of example, communication media includes wired media such as a wired network or direct-wired connection, and wireless media such as acoustic, radio frequency, infrared, and other wireless media. In some embodiments, communication media is transitory media. Combinations of any of the above are also included within the scope of computer readable media.

In some embodiments, the surface hardness evaluation system is a part of the data collection device 122 (shown in FIG. 2) or the computing device 138 (shown in FIG. 3). The computing device 138 (shown in FIG. 3) can be part of the data collection vehicle 132, the mobile hardness measurement device 134, or the movable sensor 136 in various possible embodiments.

In another example embodiment, the surface hardness evaluation system is a separate device. In some embodiments, data is transferred from the data collection device 122, the movable sensor 136, or the computing device 138 to the separate surface hardness evaluation system. The data transfer can occur through a physical transfer of data on a computer-readable storage device, such as a flash drive, or through an electronic data transfer, such as across a data communication network, such as the Internet. Electronic data transfer can occur through wired data communication or wireless data communication, or a combination wired and wireless data communication. Examples of wireless data communication are described herein, and include Wi-Fi communication, cellular communication, and other electromagnetic or optical data communication technologies. Data can be transferred as collected, after completion of a portion of the data collection, or after the completion of all of the data collection. Further, data can be transferred prior to processing of the data or after processing of the data.

FIG. 7 is an example map display 262 graphically depicting the collected data 142, to permit visual evaluation of the ground surface hardness values. In some embodiments, the map display 262 is generated by a surface hardness evaluation system, such as including computing device 200, shown in FIG. 6.

In some embodiments, data evaluation operation 142 involves graphically plotting data points 142 on a map of the site S1. To do so, a map of the site S1 is obtained, and then positions of the data points 142 are identified on the map in the appropriate locations.

For example, the GPS coordinates for a first point are used to identify the location of the first point on the map. The location of the second point is similarly identified using the GPS coordinate for the second point.

As another example, if GPS coordinates are not available, or if the map is not associated with GPS coordinates, a position of a first point can be visually identified on the map, and subsequent points can be determined based on a known sampling distance from the first point. For example, if the first data point is known to have been sampled at a southwest corner of site S1, the location of the southwest corner can be identified on the map. If it is further known that sampling then proceeded due north at 10 foot intervals, the locations of subsequent points can be determined or estimated on the map.

In some embodiments, ground surface hardness values are displayed on the map in a numeric form. In another possible embodiment, the ground surface hardness values are displayed upon mouse-over, or upon clicking on a data point.

In yet another embodiment, and as illustrated in FIG. 7, ground surface hardness values are graphically depicted using a graphical element. In this example, the graphical element is a circle, where the diameter of the circle is proportional to the ground surface hardness value. In other words, a data point having a greater ground surface hardness value is depicted with a circle having a diameter that is larger than a data point having a lower ground surface hardness value.

In yet another possible embodiment, graphical elements include different colors, where the colors are associated with hardness values. For example, a first color (e.g., red) is used to display data points having relatively high hardness values, and a second color (e.g., green) is used to display data points having relatively low hardness values. Multiple colors can be used, with each color used to represent different ranges of hardness values.

In some embodiments, the map display 262 is displayed on a display device of the surface hardness evaluation system, such as the display device 242 of the computing device 200 shown in FIG. 6. Upon display, a user can evaluate the data points, such as to identify particular regions of the site S1 that require treatment, and to prescribe an appropriate treatment, if necessary.

In this example, the map display 262 shows that hardness values at the sidelines (left and right sides of the map display 262 in FIG. 7) of site S1 are much harder than most of the rest of the site S1. It also indicates that the hardness values are elevated generally along a longitudinal centerline of the site S1 (about midway between the sidelines). The region at and around the 50 yard line has particularly high hardness values. In view of this information, localized treatment can be prescribed for the identified regions to reduce the hardness of the ground surface at these areas.

Figure 8:
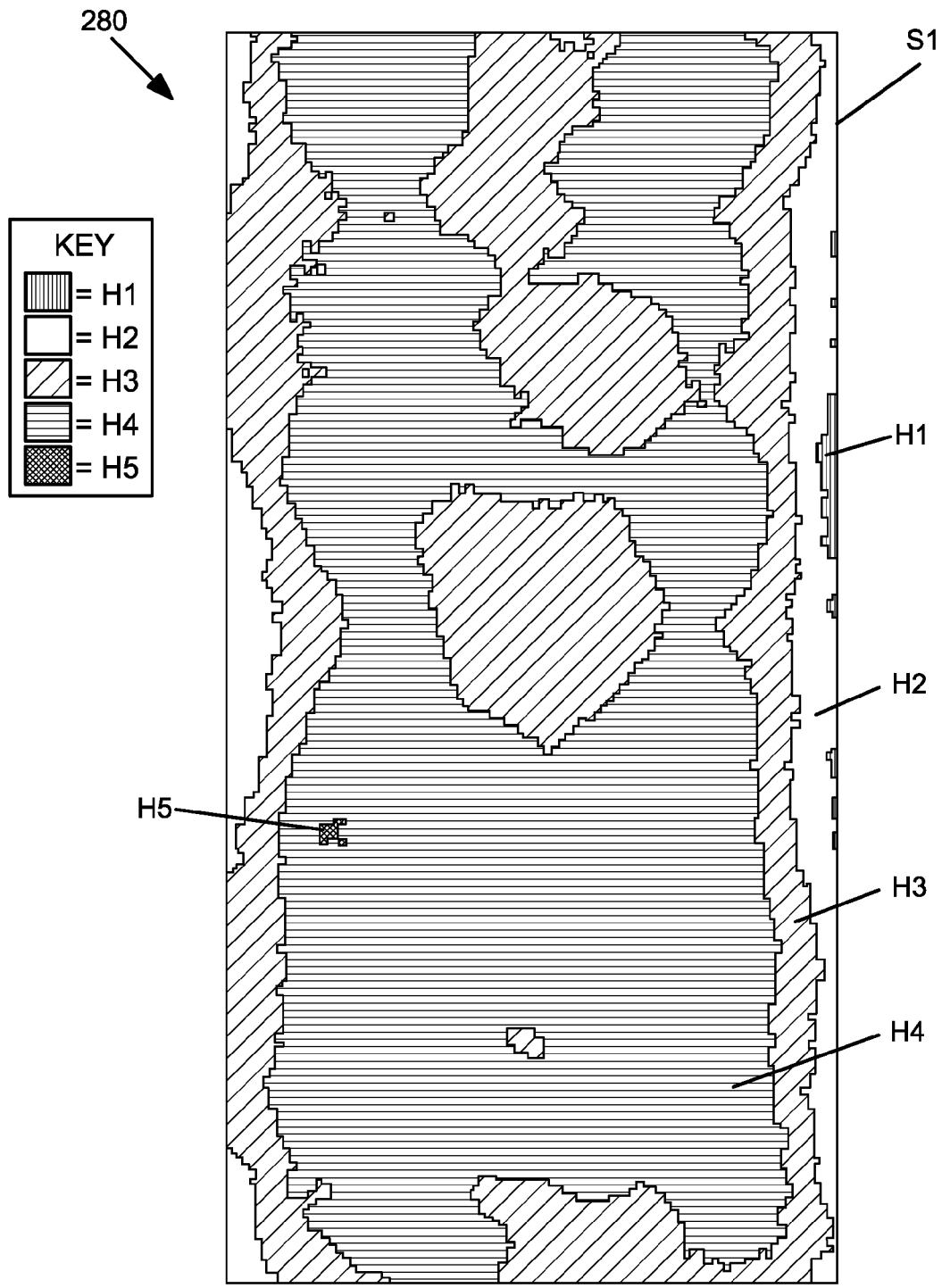
FIG. 8 is another map display graphically depicting the collected data.

FIG. 8 is another example map display 280 graphically depicting the collected data. In this example, the map display 280 shows collected data as well as interpolated data.

In some embodiments, an operation of the surface hardness evaluation system (as part of the data evaluation operation 104, shown in FIG. 1) is to generate and, if desired, display interpolated data. Interpolated data provides improved resolution of the data points. As shown in FIG. 4, even when using a surface hardness measurement device 134, the data points may still have a relatively high granularity. In other words, the available data points may still be separated by a significant distance, such as 5 to 15 feet, with unknown ground surface hardness values in-between. An approximation of the ground surface hardness conditions between the collected data points can be obtained by interpolating between the data points.

A variety of different interpolation algorithms are used in the various possible embodiments. For example, linear interpolation can be used to assign values to interpolated data points between the collected data points. Polynomial or spline interpretation is used in other embodiments. Some embodiments utilize geostatistical interpolation techniques, such as Kriging. Kriging assumes a spatial relationship between the data, and therefore compares data points with adjacent data points when computing the interpolated data points.

Once the interpolated data has been computed, the data can be graphically represented on a map display 280. The map display 280 graphically illustrates the hardness value for each data point using colors associated with ranges of hardness values. In this example, the data point values are assigned to five colors. The first color H1 (e.g., red) is used to display data points having hardness values above a certain value. The second color H2 (e.g., white) is used to display data points with a lower hardness value. The third color H3, fourth color H4, and fifth color H5 similarly depict data points having progressively lower hardness values, with the fifth color H5 representing the softest areas of the site S1. Any quantity of colors can be used, as desired. For example, the quantity of colors is in a range from 3 to 10. In other possible embodiments, tens, hundreds, or even thousands of colors are used.

In some embodiments, the map display 280 is displayed to the user, allowing the user to view the interpolated hardness data. In another possible embodiment, the surface hardness evaluation system automatically identifies the different regions of the site S1 and utilizes the data to identify those regions where treatment may be desired. For example, the region depicted with the first color H1 can be identified as a region that requires softening. Depending on the particular values, the region depicted with the second color H2 may also be identified as requiring softening. Alternatively, or in addition, the region depicted with the fifth color H5 may be too soft. If so, the system can prescribe a treatment to harden region H5, in some embodiments.

The map display 280 shown in FIG. 8 shows how the ground surface hardness has a pattern that appears to be follow the longitudinal length of the site S1. For example, the region depicted with the fourth color H4 has left and right boundaries that are somewhat linear in a direction parallel with the longitudinal length of the site S1. It is possible that this indicates that the ground surface hardness may be at least partially a function of the irrigation system. In some embodiments, the surface hardness evaluation system compares the data points to other data as part of the evaluation. For example, the locations of the sprinkler heads can be used to look for correlations between the locations of sprinkler heads and the ground surface hardness. In this example, the surface hardness evaluation system may determine that the data points shown in the region depicted by color H4 tend to be close to sprinkler heads that run longitudinally along the site S1, while data points in regions depicted with colors H1, H2, and H3 tend to be further from the sprinkler heads. Once a correlation is identified, the information can be used in determining an effective treatment plan, which may include adjustment of the irrigation system to provide additional water to regions depicted with colors H1, H2, and H3.

Similarly, if the evaluation reveals that a sprinkler head is positioned at or near to the region depicted with color H5, the surface hardness evaluation system may determine that the wetness of the region is likely to require adjustment of the irrigation system. For example, the sprinkler head may be supplying too much water to the region, causing the ground surface to be too soft. Accordingly, the system can prescribe treatment to fix or adjust the sprinkler head at this location, in some embodiments.

Similarly, the surface hardness evaluation system utilizes additional data in some embodiments to evaluate a site and to determine an appropriate treatment plan. Another example is illustrated in FIG. 9.

In another possible embodiment, the surface hardness evaluation system computes standard deviations of data points, and generates a map display, similar to that shown in FIG. 8, that graphically depicts the values of the standard deviations, rather than the actual values of the data points or interpolated data points.

FIG. 9 illustrates an example method of prescribing treatment using hardness data. In this example, the surface hardness evaluation system utilizes moisture data to look for a correlation between moisture data and hardness data, when prescribing treatment options.

In some embodiments, the surface hardness evaluation system utilizes other data in addition to the hardness data to identify an appropriate treatment plan. In this example, the system begins by evaluating the hardness data as shown in FIG. 8 or 9, and identifies regions of a site 51 having hardness values that are outside of a desired range of values. These regions are flagged as regions in which treatment may be desired.

Once the regions requiring treatment are identified, additional data is evaluated to determine what type of treatment is the most appropriate. For example, the data is evaluated to determine whether there is a correlation between the hardness data and moisture data. The moisture data can be obtained during the data collection operation by using a soil moisture sensor, for example. If the surface hardness evaluation system determines that there is a correlation, one option for treatment may be an adjustment of the irrigation system. By increasing the amount of water supplied to a region, it may be possible to soften the ground surface in that region. Similarly, by reducing the amount of water supplied to a region, it may be possible to harden the ground surface in that region.

Referring to the chart in FIG. 9, if a region has been identified as having hardness values that are above a desired threshold value, the system then evaluates the moisture values in that region to determine whether the hardness is a result of the ground surface being too dry. If a correlation is found, the system can suggest increasing the amount of water supplied to the region. In some embodiments, the system provides suggested adjustments that could be made to the operating parameters of the irrigation system (e.g., an adjustment of the duration or frequency of irrigation), or may suggest a physical reconfiguration of the irrigation system.

Similarly, if a region is found to be too soft, the system determines whether there is a correlation between the softness of the ground surface and the moisture content of the ground surface in that region. If so, the system can suggest treating the condition by adjusting the irrigation systems operating parameters or physical reconfiguration of the irrigation system.

If a correlation is not found between the hardness and the moisture data, the system determines that the condition is probably not caused by the irrigation system. Accordingly, the system prescribes alternative treatments. For example, if the hardness data indicates that the ground surface is too hard, and the moisture data indicates that the ground surface is either too wet or within a desired range of moisture values, the system can prescribe a treatment to soften the ground surface. For example, the ground surface may need to be aerated or tilled. An adjustment in the composition of the ground surface may also be appropriate, such as to adjust the content of organic matter, sand, clay, or synthetic materials.

If the hardness data indicates that the ground surface is too soft, and the moisture data indicates that the ground surface is either too dry or within a desired range of moisture values, the system can prescribe a treatment to harden the ground. For example, the ground surface may need to be compacted. Alternatively, the composition of the ground surface may be necessary, such as to adjust the content of organic matter, sand, clay, or synthetic materials.

When the ground surface includes artificial turf, the ground surface can be similarly be modified to adjust the hardness of the ground surface in selected regions. For example, if a region is determined to be too hard, infill such as crumb rubber can be supplied to that region to soften the ground surface. If a region is determined to be too soft, sand can be added to harden the ground surface.

In some embodiments, the mobile data collection device 130 (shown in FIG. 3) includes one or more of a sand spreading device and an infill spreading device, and includes one or more containers for storing sand and/or infill. The mobile data collection device 130 can be programmed to automatically spread sand and/or infill based at least in part upon the ground surface hardness measurements. For example, if the $G_{MAX}$ value exceeds a predetermined maximum value (e.g., 100 G's) the mobile data collection device 130 activates the infill spreading device to supply infill to that location of the site. If the $G_{MAX}$ value is less than a predetermined value, the sand spreading device is activated to supply sand to that location of the site.

Figure 10:
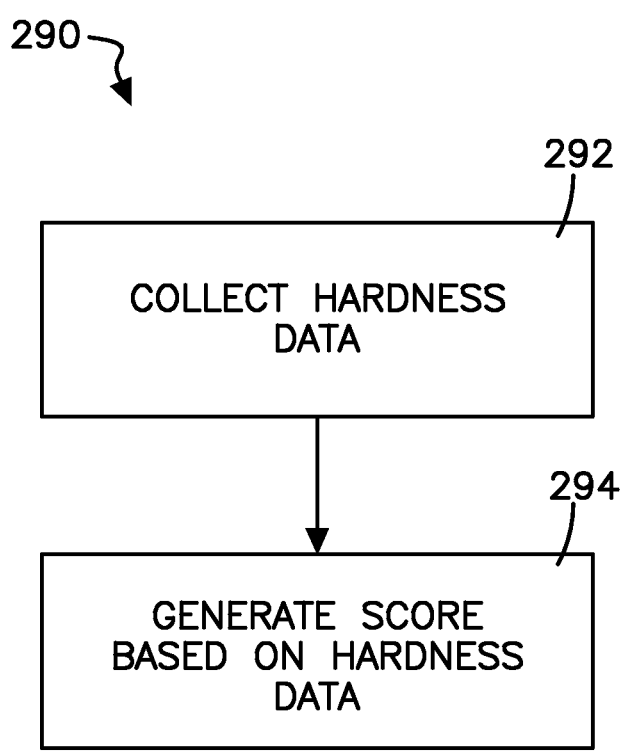
FIG. 10 is a flow chart illustrating an exemplary method of evaluating ground surface hardness for a site.

FIG. 10 is a flow chart illustrating an exemplary method 290 of evaluating ground surface hardness for a site. In this example, method 290 includes an operation 292 and an operation 294.

The operation 292 is performed to collect hardness data. The hardness data is preferably collected by a mobile data collection device 130, such as illustrated in FIG. 3, but could alternatively be collected by a handheld data collection device 110, as illustrated in FIG. 2. As described herein, hardness data can be collected by detecting acceleration of a hammer or other object as it impacts the ground surface at sample locations in the site. In some embodiments, the ground surface hardness values are the maximum acceleration measurements recorded for each impact ($G_{MAX}$) at each sample location.

The operation 294 is then performed to generate a score based at least in part upon the collected hardness data. In some embodiments, the score is a single numerical value assigned to the site that is at least partially representative of the ground surface hardness at the site.

An example of the score is an average of the $G_{MAX}$ values collected for the site.

Another example of the score indicates the percentage of the site that has a ground hardness value that exceeds a predetermined threshold value. For example, the percentage of the area of the site that has a ground surface value of greater than (or greater than or equal to) the threshold value (e.g., 100 G's). The score can be computed in another embodiment as the percentage of the area of the site that has a ground surface hardness value of less than (or less than or equal to) a threshold value.

Other scores are generated in other embodiments that are based at least in part on the collected hardness values, but can also be based on other information, such as soil moisture data, compaction data, or other values.

The generation of a ground surface hardness score is useful in comparing a site with other sites. In addition, ground surface hardness recommendations can be generated that identify a preferred range of ground surface hardness scores. A comparison can then be made between the generated ground surface hardness score for a particular site and the recommended ranges of ground surface hardness scores. If the ground surface hardness score does not fall within the preferred range of ground surface hardness scores, treatments can be identified to adjust the ground surface hardness so that it falls within the preferred range. Examples of such treatments are described herein.

Therefore, the scoring of a site can be helpful in evaluating the ground surface hardness of a site in a way that has not previously been available. Remedial action can then be taken in some embodiments to improve the safety and playability of the site for the intended activities. A site having a ground surface that is too soft can be hardened by compaction, reduced irrigation, or the addition of sand, for example. A site having a ground surface that is too hard can be softened by aeration, cultivation, or the addition of infill, for example. In some embodiments, only particular regions of the site that are identified as having undesired ground surface hardness conditions are treated to resolve the undesired conditions.

Figure 11:
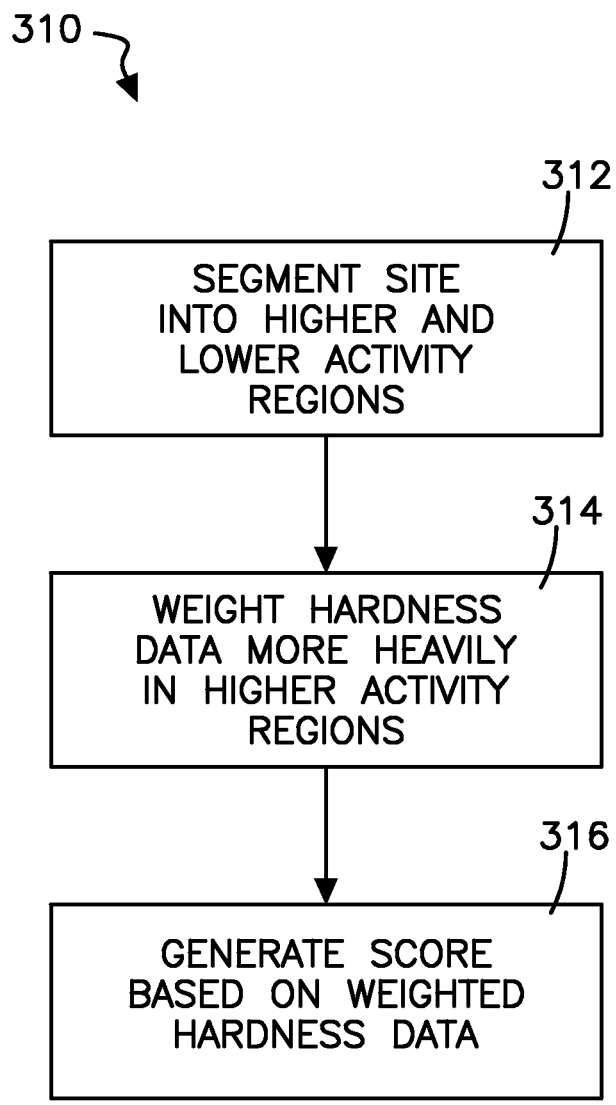
FIG. 11 is a flow chart illustrating an example method of generating a score based at least in part on hardness data.

FIG. 11 is a flow chart illustrating an example method 310 of generating a score based at least in part on hardness data. FIG. 11 is also an example of the operation 294, shown in FIG. 10. In this example, the method 310 includes operations 312, 314, and 316.

The operation 312 is performed to segment the site into at least two regions, including at least one higher activity region and at least one lower activity region. In some embodiments, the site is segmented into more than two regions, and can include more than one higher activity region, and/or more than one lower activity region.

A reason for segments is based on the understanding that the conditions of certain regions of the site that receive a greater amount of activity are more important than the conditions of other regions of the site that receive a lesser amount of activity. For example, on a sports field, the conditions of the field in areas where play most frequently occurs are more important than conditions of the field in areas where play occurs less frequently.

Examples of operation 312 are illustrated and described in more detail with reference to FIGS. 12-13.

After the site has been segmented into higher and lower activity regions, operation 314 is performed to weight the hardness data for locations within the higher activity regions more heavily than the hardness data for locations within the lower activity regions.

In some embodiments, a ground surface hardness score is computed for each of the regions identified in operation 312. Then these regional scores are multiplied by a weighting factor. In an example embodiment, the weighting factor of ⅔ is applied to the higher activity regional score, and a weighting factor of ⅓ is applied to the lower activity regional score. When there are multiple higher activity regions or multiple lower activity regions, an average of the regions can be used to generate a combined higher activity regional score and a combined lower activity regional score. Alternatively, a score for the higher activity region (or the lower activity region) can be computed as a single region, and the resulting score then multiplied by the weighting factor.

A site score is then generated in operation 316 based at least in part on the weighted hardness data computed in operation 314. For example, the score can be computed as the sum of the weighted higher activity regional scores and the weighted lower activity regional scores. Other formulas can be used to generate a site score, which may utilize additional factors or data. Another example is illustrated and described herein with reference to FIG. 16, which includes multiple different component scores to compute the final site score.

Figure 12:
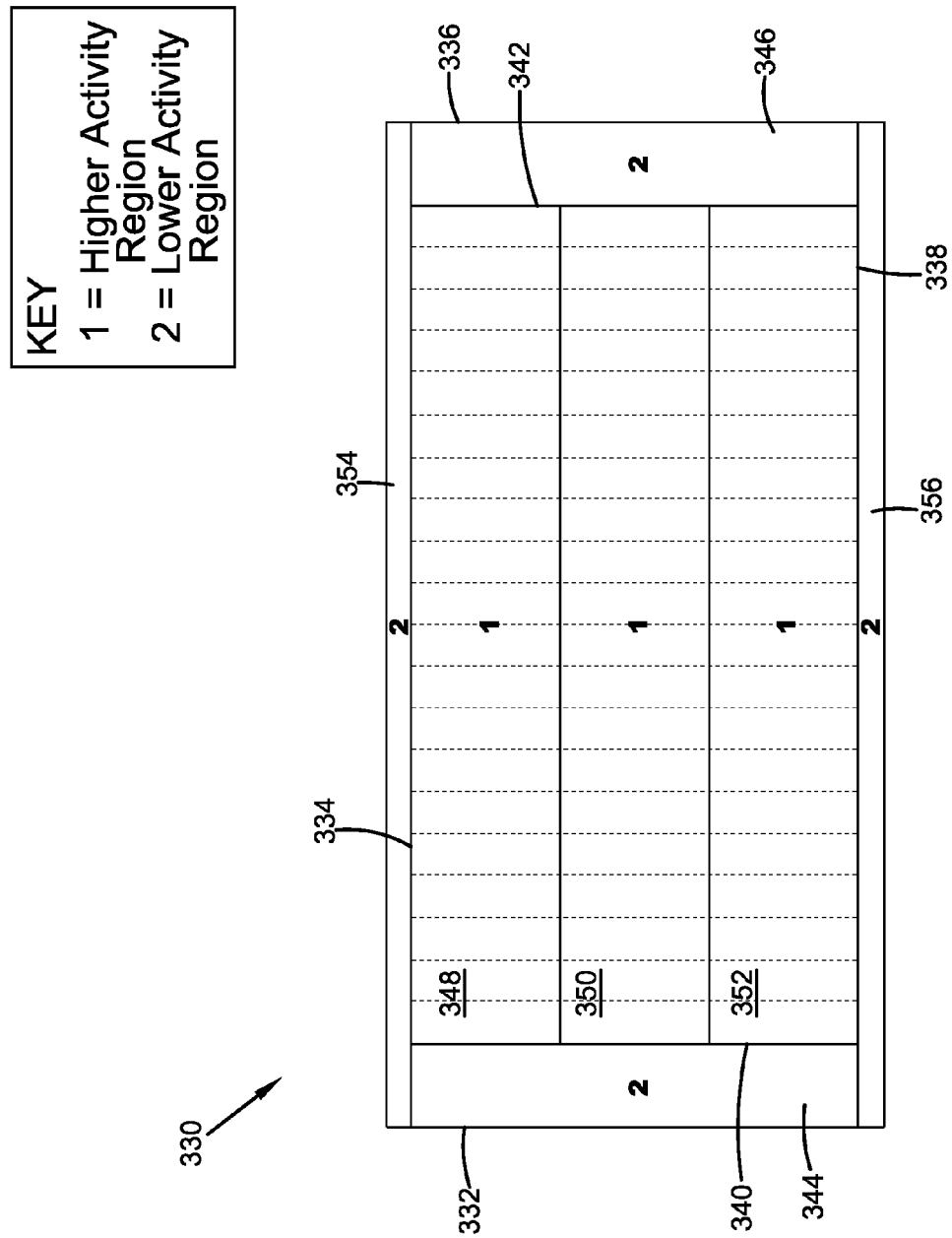
FIG. 12 is a schematic diagram of an exemplary site illustrating the segmenting the site into higher and lower activity regions.

FIG. 12 is a schematic diagram of an exemplary site illustrating the segmenting of the site into higher and lower activity regions. In this example, the site is an American football field 330 including boundary lines 332, 334, 336, and 338, goal lines 340 and 342, end zones 344 and 346, field regions 348, 350, and 352, and edge regions 354 and 356.

In this example, the football field 330 has been segmented into multiple regions including end zones 344 and 346, field regions 348, 350, and 352, and edge regions 354. For each region, a determination was made as to whether the respective region is a higher activity region ("1") or a lower activity region ("2"). The field regions 348, 350, and 352 were identified as higher activity regions, and the end zones 344 and 346, and edge regions 354 (outside of the boundary lines 334 and 336) were identified as lower activity regions.

Figure 13:
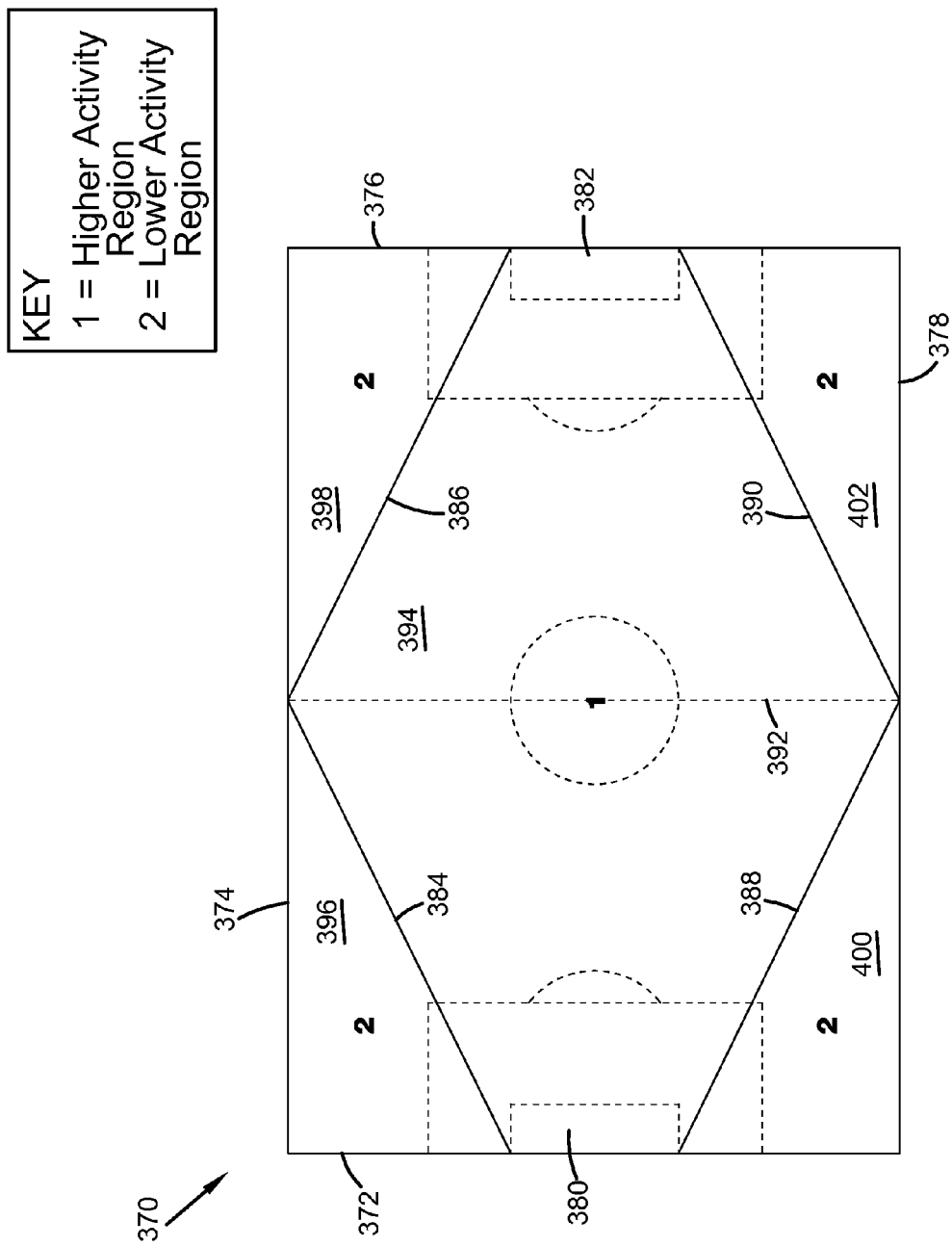
FIG. 13 is a schematic diagram of another exemplary site illustrating the segmenting the site into higher and lower activity regions.

FIG. 13 is a schematic diagram of another exemplary site illustrating the segmenting of the site into higher and lower activity regions. In this example, the site is a soccer field 370 including boundary lines 372, 374, 376, and 378 and goals 380 and 382.

In this example, it was determined that the highest concentration of activity in the soccer field 370 is within a central region, and that the play funnels in toward the goals 380 and 382. As a result, less play occurs in corner regions. Accordingly, a central higher activity region 394 was defined as the space between the goals 382 that is bounded by diagonal lines 384, 386, 388, and 390 that extend from edges of the goals 380 and 382 and out to edges of the midfield line 392. Corner lower activity regions were also defined, including regions 396, 398, 400, and 402.

In some embodiments, more than two activity regions can be defined. For example, a site could be divided into three regions, including a higher activity region, a lower activity region, and a medium activity region.

Once the site has been segmented into the respective regions, statistics can be computed for each region. In some embodiments, the collected data is used directly, while in other embodiments the collected data is interpolated to a higher resolution, such as illustrated in FIG. 8 or 14.

In some embodiments, a score is generated for each region. An example of a score is the percentage of data points (collected or interpolated) that meet a predetermined criterion. An example of such a criterion is hardness values greater than a threshold value. Another example of such a criterion is hardness values less than a threshold value. An example is illustrated and described in more detail with reference to FIG. 14.

Some fields are used for multiple different activities. For example, the football field 330 and the soccer field 370 may both be the same field. However, the importance of ground hardness characteristics of the field can be different depending on the desired activity. For example, if the corner region 396 has excessive hardness, the hardness may be less of an issue during a soccer game (where the corner regions have tend to have less activity) than in a football game (where the corner regions may have greater activity). Accordingly, in some embodiments the evaluation of the site involves first identifying a type of activity of interest, and then evaluating the characteristics of the field for that particular activity. Different hardness scores can therefore be generated for the same field, depending on the activity, as described in more detail herein.

Figure 14:
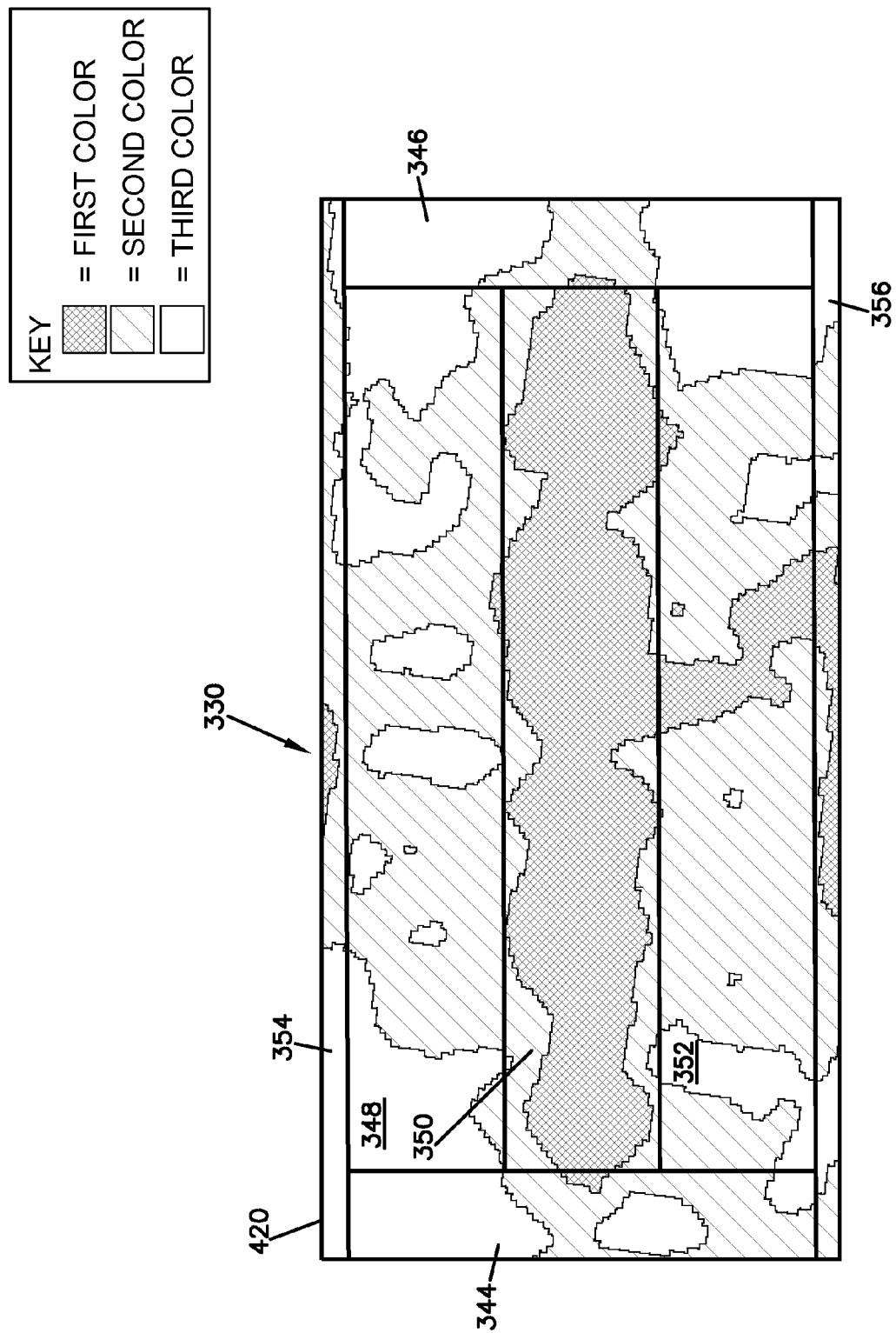
FIG. 14 is an example map display for another exemplary site, illustrating collected and interpolated hardness data.

FIG. 14 is an example map display 420 for another exemplary site. The map display 420 illustrates the collected and interpolated hardness data for the various regions of an American football field 330 (such as described with reference to FIG. 13). The data displayed in FIG. 14 is not the same data as displayed in FIG. 8.

In this example, the hardness data is displayed with three colors. A first color (e.g., red) represents data having a value greater than a threshold value (e.g., 100 G's). These locations of the field 330 are considered to have excessive hardness. A second color (e.g., pink) represents data having a value less than but near to the threshold value. For example, the data may be within 10% of the threshold value. These locations of the field 330 are considered to have borderline hardness. A third color (e.g., white) represents data having a value that is sufficiently less than the threshold value, such as below the range of the borderline hardness values (e.g., less than 90% of the threshold value).

In some embodiments, a percentage of the higher activity region that exceeds the threshold value is then computed. In this example, it is found that 29% of the higher activity region (including regions 348, 350, and 352) exceed the threshold value (as shown as the area having the first color). It is also found that 7% of the lower activity region (including regions 344, 346, 354, and 356) exceed the threshold value (also shown with the first color).

In some embodiments, these values can then be weighted according to the activity level when generating a final score for the site so that excessive hardness in the higher activity region results in a greater reduction in the score than excessive hardness in the lower activity region.

Figure 15:
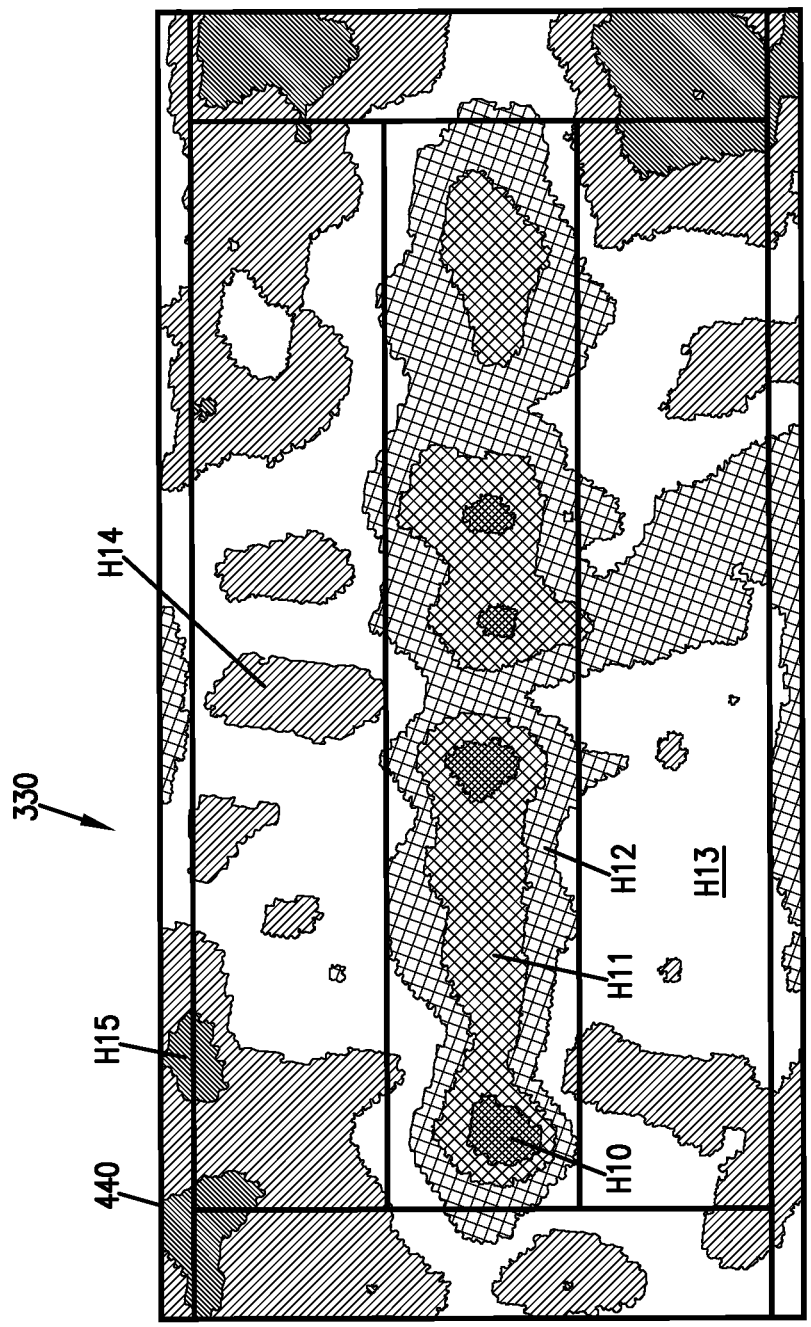
FIG. 15 is another example map display illustrating the standard deviations of the hardness data.

FIG. 15 illustrates another map display 440 of the football field 330. In this example, the map display 440 displays the standard deviations of the hardness data across the site. In this example, the standard deviation data is displayed with multiple different colors, where each color represents a range of standard deviation values. In this example, a total of 7 colors are used, including three shades of a first color H10, H11, and H12 (e.g., dark red to light red), a second color H13 (e.g., white), and three shades of a third color H14, H15, and H16 (e.g., light blue to dark blue). No data sets had the standard deviations represented by color H16, and so this color is not included in FIG. 15. The colors identify regions of the site 330 having values that have the greatest standard deviation values H10, to those that have the least standard deviation values H16.

Figure 16:
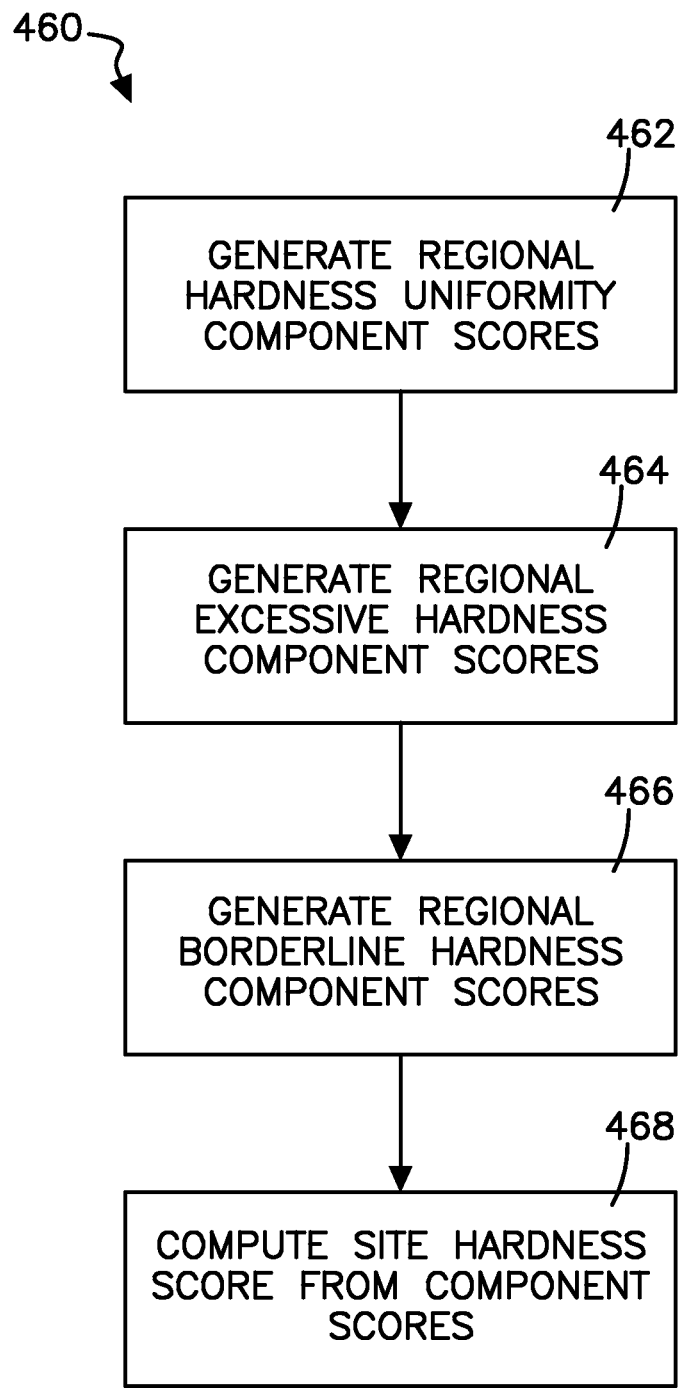
FIG. 16 is a flow chart illustrating another exemplary method of computing a ground surface hardness score for a site.

FIG. 16 is a flow chart illustrating another exemplary method 460 of computing a ground surface hardness score for a site. In this example, the method 460 includes the generation of multiple component scores for each activity region. In some embodiments, a ground surface hardness score for the site is then computed based at least in part on the component scores. Method 460 includes operations 462, 464, 466, and 468, in some embodiments.

Operation 462 involves generating regional hardness uniformity scores. The hardness uniformity score provides a score representative of how uniform the hardness of the playing surface is across a region.

An example will now be provided. In this example, maximum and minimum standard deviations are defined for values within a given region (e.g., higher activity region or lower activity region). The algorithm compares actual standard deviations of values within the region to a minimum and a maximum value. Table 1 illustrates an exemplary set of maximum and minimum standard deviation values, although other embodiments can use other values.

TABLE 1

| Region | Min. Standard Dev. | Max. Standard Deviation |
|---|---|---|
| Higher Activity | 3.0 | 9.0 |
| Lower Activity | 4.0 | 10.0 |

In this example, the higher activity region is assigned a minimum standard deviation of 3.0 and a maximum standard deviation of 9.0. The lower activity region is assigned a minimum standard deviation of 4.0 and a maximum standard deviation of 10.0. These values were selected in this example based on an expected mean of 80 (the approximate average of the available datasets.

The actual standard deviation values are then compared with the minimum and maximum standard deviation values listed in Table 1.

If the standard deviation of a region is greater than the maximum standard deviation, a score of 0 is given to that region. If the standard deviation of a region is less than the minimum standard deviation, a score of 10 is given to that region. If the standard deviation is between or equal to the minimum or the maximum standard deviation, then Equation 1 is used to compute the score:

$$\text{Score} = [(SD_{MAX} - SD)/(SD_{MAX} - SD_{MIN})] \quad \text{(Equation 1)}:$$

where $SD_{MAX}$ is the maximum standard deviation listed in Table 1 for the respective region, $SD_{MIN}$ is the minimum standard deviation listed in Table 1 for the respective region, and SD is the actual standard deviation of ground surface hardness values (including collected and interpolated values) within the region.

The result is a score from 0 to 10 indicative of the uniformity of the ground surface hardness within the region. A single numerical score can therefore be computed for the higher activity region, and another numerical score can be computed for the lower activity region.

In the example illustrated in FIGS. 14 and 15, the following scores were obtained. First, in the higher activity region, a standard deviation of 7.6 was computed. Applying Equation 1, the uniformity score for the region was 2.3((9−7.6)/(9−3))=2.3). Similarly, in the lower activity region, a standard deviation of 6.24 was computed. Applying Equation 1, the uniformity score for the region was 6.3((10−6.24)/(10−4))=6.3).

A site uniformity score can be computed by weighting the scores for each region. In this example, a weighting factor of ⅔ is applied to the higher activity region score, and a weighting factor of ⅓ is applied to the lower activity region score. Accordingly, a site uniformity score of 3.6 is computed ((⅔)* 2.3+(⅓)*6.3)=3.6).

Operation 464 is performed to generate a regional excessive hardness score. The excessive hardness score is indicative of how much of the site exceeds a threshold hardness value.

For the example site shown in FIGS. 14 and 15, a maximum hardness value is defined, such as 100 G's. Within each region, the hardness values are compared with the maximum hardness value to compute the percentage of the region that exceeds the maximum hardness value.

In an example embodiment, maximum permissible percentages are defined for each region. For example, the higher activity region is given a maximum permissible percentage of 8% and the lower activity region is given a maximum permissible percentage of 15%. Other percentages are used in other embodiments.

If the calculated percentage exceeds the maximum permissible percentage for the respective region, an excessive hardness component score of 0 is given to that region. If the calculated percentage is less than the maximum permissible percentage, then the excessive hardness component score is computed using Equation 2:

$$(1 - \%_{HARD})*10 \quad \text{(Equation 2)}:$$

where $\%_{HARD}$ is the percentage of the region having hardness values that exceed the threshold value.

In the example shown in FIGS. 14 and 15, the higher activity region was determined to have 29% of the region that exceeds the threshold value, and the lower activity region was determined to have 7% of the region that exceeds the threshold value. Because 29% exceeds the maximum permissible percentage of 8%, the higher activity region was given an excessive hardness component score of 0. The lower activity region has a percentage below the maximum permissible percentage of 15%, and therefore the excessive hardness component score of 9.3 was computed using Equation 2 ((1− 0.07)*10=9.3).

A site excessive hardness component score can be computed by weighting the scores from the higher activity region and the lower activity region, as discussed with reference to operation 462. In this example, a site excessive hardness component score of 3.6 is computed (($\frac{2}{3}$)*0+($\frac{1}{3}$)*9.3=3.1).

Operation 466 is performed in some embodiments to generate a regional borderline hardness score indicative of the percentage of the region that has a hardness that is near to the threshold hardness value.

In this example, the borderline hardness component scores are computed for each region using a borderline threshold value. In some embodiments, the borderline threshold value is 90% of the excessive hardness threshold value. For an excessive hardness threshold value of 100 G's, for example, the borderline threshold value is 90 G's. Other thresholds are used in other embodiments.

The borderline component score is then computed as the percentage of the points in the region that are less than or equal to the borderline threshold value, multiplied by 10. A high percentage of points that are between the borderline threshold value and the excessive hardness threshold value, will therefore result in a lower score. This can be helpful to identify fields that do not quite exceed the threshold values, but are very close to the hardness threshold.

In the example shown in FIGS. 14 and 15, the percent of hardness values in the higher activity region that exceeded the borderline threshold value was 20%, and the percent in the lower activity region was 52%. Accordingly, the higher activity region is given a borderline hardness component score of 2(0.20*10=2) and the lower activity region is given a borderline hardness component score of 5.2(0.52*10=5.2).

A site borderline component score can similarly be computed by weighting the regional scores. In the example shown in FIGS. 14 and 15, the site borderline component score is 3.1(($\frac{2}{3}$)*2+($\frac{1}{3}$)*5.2=3.1).

In some embodiments, the component scores computed in operations 462, 464, and 466 are then combined to generate a site hardness score based on the component scores.

In some embodiments, the site score is based upon a weighting of the different component scores. Exemplary weighting values are shown in Table 2.

TABLE 2

| Component Score | Weighting Value |
| --- | --- |
| Uniformity | 30% |
| Excessive Hardness | 50% |
| Borderline Hardness | 20% |

The weighting values represent the contribution that each component should have on the final hardness scores. Other weighting values can be used in other embodiments. In addition, some embodiments utilize additional factors to compute the site hardness score.

In the example shown in FIGS. 14 and 15, the component scores are combined to generate a final site hardness score of 3.3 using the weighting values shown in FIG. 2 (0.30*3.6+0.50*3.1+0.20*3.1=3.3).

In some embodiments, a site scorecard is generated that displays the regional, component, and site scores. An example of a site scorecard is shown in Table 3 including data from the example site shown in FIGS. 14 and 15.

TABLE 3

| | Higher Activity Region | Lower Activity Region | Component Score |
| --- | --- | --- | --- |
| Uniformity | 2.3 | 6.3 | 3.6 |
| Excessive Hardness | 0 | 9.3 | 3.1 |
| Borderline Hardness | 2 | 5.2 | 3.1 |
| Total Scores | 1.1 | 7.6 | 3.3 |

The various embodiments described above are provided by way of illustration only and should not be construed to limit the claims attached hereto. Those skilled in the art will readily recognize various modifications and changes that may be made without following the example embodiments and applications illustrated and described herein, and without departing from the true spirit and scope of the following claims.

What is claimed is:

1. A method of evaluating ground surface hardness for a site, the method comprising:
   collecting acceleration data using a ground surface hardness measurement device including a movable sensor by dropping the movable sensor onto a ground surface at sample locations within the site;
   generating a plurality of values, each value representative of ground surface hardness for each of the sample locations based on the acceleration data;
   generating, using at least one computing device, a single score for at least a portion of the site based at least in part upon the plurality of values for the sample locations, the single score at least partially representative of a ground surface hardness of the at least a portion of the site; and
   segmenting the site into at least two regions, including at least one higher activity region and at least one lower activity region; and
   weighting the values representative of ground surface hardness for the at least one higher activity region more heavily than the values for the at least one lower activity region, wherein generating the single score uses the weighted values.

2. The method of claim 1, wherein generating, using at least one computing device, a single score comprises generating a single numerical score for each of the at least one higher activity region and the at least one lower activity region based at least in part on maximum acceleration values of the site locations within the respective regions.

3. The method of claim 1, further comprising:
   evaluating the values representative of ground surface hardness at the sample locations to identify at least one region of the site having an undesirable ground surface hardness condition; and
   prescribing a treatment for the undesirable ground surface hardness condition at the at least one region.

4. The method of claim 1, wherein the value representative of ground surface hardness is maximum acceleration detected during the impact of the movable sensor with the ground surface.

5. The method of claim 4, wherein generating the single score comprises generating a single numerical score for the at least a portion of the site based at least in part on at least some of the maximum acceleration values.

6. The method of claim 1, wherein generating a single score comprises:
   generating hardness uniformity component scores;
   generating excessive hardness component scores;
   generating borderline hardness component scores; and computing the single score based at least in part upon the hardness uniformity component scores, the excessive hardness component scores, and the borderline hardness component scores.

7. The method of claim 6, further comprising generating a scorecard for the site, the scorecard including at least the component scores and the single score.

8. The method of claim 1, wherein the single score indicates a percentage of the area of the site that has a ground surface hardness value that exceeds a ground surface hardness threshold.

9. The method of claim 8, wherein generating, using at least one computing device, the single score for the site comprises:
   determining, the at least one computing device, the ground surface hardness threshold;
   comparing, using the at least one computing device, the values for the sample locations with the ground surface hardness threshold value; and
   generating, using the at least one computing device, the single score for the site based at least in part upon the comparison.

10. The method of claim 1, wherein the single score indicates a hardness uniformity of the at least portion of the site.

11. The method of claim 10, wherein generating, using at least one computing device, the single score comprises:
   determining, using the at least one computing device, a maximum standard deviation and a minimum standard deviation;
   calculating, using the at least one computing device, a standard deviation of the values for the sample locations;
   comparing, using the at least one computing device, the standard deviation of the values with the maximum and minimum standard deviations; and
   generating, using the at least one computing device, the single score for the site based at least in part upon the comparison.

12. The method of claim 1, further comprising:
   generating a map display with a computing device, the map display graphically displaying the values representative of the ground surface hardness at the sample locations.

13. The method of claim 12, wherein the map display includes graphical elements, wherein the graphical elements visually indicate a magnitude of the values representative of the ground surface hardness at the sample locations.

14. The method of claim 12, wherein the map display further depicts interpolated ground surface hardness data.

15. A method of evaluating ground surface hardness for a site, the method comprising:
   collecting acceleration data using a ground surface hardness measurement device including a moveable sensor by dropping the movable sensor onto a ground surface at sample locations;
   generating a plurality of values, each value representative of ground surface hardness for each of the sample locations based on the acceleration data; and
   generating, using at least one computing device, a single score for at least a portion of the site based at least in part upon the plurality of values for the sample locations, the single score at least partially representative of a hardness uniformity of the at least a portion of the site, wherein generating the single score for the site comprises:
      determining, using the at least one computing device, a maximum standard deviation and a minimum standard deviation;
      calculating, using the at least one computing device, a standard deviation of the values for the sample locations;
      comparing, using the at least one computing device, the standard deviation of the values with the maximum and minimum standard deviations; and
      generating, using the at least one computing device, the single score for the at least a portion of the site based at least in part upon the comparison.

16. A method of evaluating ground surface hardness for a site, the method comprising:
   using a mobile data collection device to automatically drop an object including an accelerometer onto a ground surface at sample locations spaced at regular intervals within the site;
   detecting acceleration of the object with the accelerometer as the object impacts the ground surface at the sample locations;
   generating a value representative of ground surface hardness for each of the sample locations, wherein the value representative of ground surface hardness is a maximum acceleration detected during the impact of the object with the ground surface;
   generating a single numerical score for the site based at least in part on at least some of the maximum acceleration values;
   segmenting the site into at least two regions, including at least one higher activity region and at least one lower activity region; and
   weighting the values representative of ground surface hardness for the at least one higher activity region more heavily than the values for the at least one lower activity region, wherein generating the single numerical score uses the weighted values.

17. The method of claim 16, further comprising generating a single numerical score for each of the at least one higher activity regions and the at least one lower activity regions based at least in part on maximum acceleration values of the site locations within the respective regions.

18. A method of evaluating ground surface hardness for a site, the method comprising:
   using a mobile data collection device to automatically drop an object including an accelerometer onto a ground surface at sample locations spaced at regular intervals within the site;
   detecting acceleration of the object with the accelerometer as the object impacts the ground surface at the sample locations;
   generating a value representative of ground surface hardness for each of the sample locations, wherein the value representative of ground surface hardness is a maximum acceleration detected during the impact of the object with the ground surface; and
   generating a single numerical score for the site based at least in part on at least some of the maximum acceleration values, wherein generating the single numerical score for the site comprises:
      generating hardness uniformity component scores;
      generating excessive hardness component scores;
      generating borderline hardness component scores; and
      computing the single numerical score based at least in part upon the hardness uniformity component scores, the excessive hardness component scores, and the borderline hardness component scores.

19. The method of claim 18, further comprising generating a scorecard for the site, the scorecard including at least the component scores and the single numerical score.

20. A method of evaluating ground surface hardness for a site, the method comprising:

collecting acceleration data using a ground surface hardness measurement device including a movable sensor by dropping the movable sensor onto a ground surface at sample locations within the site;

generating a plurality of values, each value representative of ground surface hardness for each of the sample locations based on the acceleration data; and generating, using at least one computing device, a single score for at least a portion of the site based at least in part upon the plurality of values for the sample locations, the single score at least partially representative of a ground surface hardness of the at least a portion of the site, wherein generating a single score comprises:

generating hardness uniformity component scores;
generating excessive hardness component scores;
generating borderline hardness component scores; and
computing the single score based at least in part upon the hardness uniformity component scores, the excessive hardness component scores, and the borderline hardness component scores.

21. The method of claim 20, further comprising generating a scorecard for the site, the scorecard including at least the component scores and the single score.

* * * * *